US009117273B2

(12) United States Patent
Sibarita

(10) Patent No.: US 9,117,273 B2
(45) Date of Patent: Aug. 25, 2015

(54) METHOD AND APPARATUS FOR SINGLE-PARTICLE LOCALIZATION USING WAVELET ANALYSIS

(71) Applicant: Jean-Baptiste Sibarita, Bordeaux Cedex (FR)

(72) Inventor: Jean-Baptiste Sibarita, Bordeaux Cedex (FR)

(73) Assignees: Centre National de la Recherche Scientifique (CNRS), Paris (FR); Universite de Bordeaux, Bordeaux (FR)

(*) Notice: Subject to any disclaimer, the term of this patent is extended or adjusted under 35 U.S.C. 154(b) by 135 days.

(21) Appl. No.: 13/741,606

(22) Filed: Jan. 15, 2013

(65) Prior Publication Data

US 2013/0294645 A1  Nov. 7, 2013

(30) Foreign Application Priority Data

May 2, 2012  (EP) .................................... 12166450

(51) Int. Cl.
*G06T 7/00* (2006.01)
*G02B 21/36* (2006.01)
(Continued)

(52) U.S. Cl.
CPC ............ *G06T 7/004* (2013.01); *G01N 21/6458* (2013.01); *G02B 21/0076* (2013.01);
(Continued)

(58) Field of Classification Search
CPC .............. G06K 9/00516; G06K 9/526; G06K 9/00127; G06K 9/0014; G06K 2009/488; G06K 2009/58; G01N 15/10; G01N 15/1463; G01N 15/1475; G06T 7/004; G06T 2207/10056; G06T 2207/10064; G06T 2207/20064

USPC ........ 382/128, 133, 173, 276; 356/4.05, 4.09, 356/336, 337, 342
See application file for complete search history.

(56) References Cited

U.S. PATENT DOCUMENTS 7,342,717 B1 * 3/2008 Hausmann et al. ........... 359/370
8,212,866 B2 * 7/2012 Lemmer et al. ................ 348/79
(Continued)

FOREIGN PATENT DOCUMENTS

WO     WO2012039636 A2 *  3/2012 ............. G02B 21/16

OTHER PUBLICATIONS

Olivo-Marin, Jean-Cristophe. "Extraction of spots in biological images using multiscale products." Pattern Recognition. 35. (2002): 1989-1996. Print.*

(Continued)

*Primary Examiner* — Michael A Newman
(74) *Attorney, Agent, or Firm* — John D. Lanza; Foley & Lardner LLP

(57) ABSTRACT

Accurate localization of isolated particles is important in single particle based super-resolution microscopy. It allows the imaging of biological samples with nanometer-scale resolution using a simple fluorescence microscopy setup. Nevertheless, conventional techniques for localizing single particles can take minutes to hours of computation time because they require up to a million localizations to form an image. In contrast, the present particle localization techniques use wavelet-based image decomposition and image segmentation to achieve nanometer-scale resolution in two dimensions within seconds to minutes. This two-dimensional localization can be augmented with localization in a third dimension based on a fit to the imaging system's point-spread function (PSF), which may be asymmetric along the optical axis. For an astigmatic imaging system, the PSF is an ellipse whose eccentricity and orientation varies along the optical axis. When implemented with a mix of CPU/GPU processing, the present techniques are fast enough to localize single particles while imaging (in real-time).

33 Claims, 16 Drawing Sheets

(51) Int. Cl.
*G01N 21/64* (2006.01)
*G02B 21/00* (2006.01)

(52) U.S. Cl.
CPC ............ *G02B21/365* (2013.01); *G06T 7/0042* (2013.01); *G06T 7/0081* (2013.01); *G06T 7/0095* (2013.01); *G06T 2207/20064* (2013.01)

(56) References Cited

U.S. PATENT DOCUMENTS

| | | | | |
|---|---|---|---|---|
| 8,564,792 | B2* | 10/2013 | Zhuang et al. | 356/624 |
| 8,624,986 | B2* | 1/2014 | Li | 348/208.13 |
| 2008/0068589 | A1* | 3/2008 | Hess et al. | 356/36 |
| 2008/0137059 | A1* | 6/2008 | Piestun et al. | 356/4.01 |
| 2009/0219549 | A1* | 9/2009 | Nishizaka et al. | 356/620 |
| 2010/0008597 | A1* | 1/2010 | Findlay et al. | 382/275 |
| 2010/0181497 | A1* | 7/2010 | Hess et al. | 250/459.1 |
| 2011/0002530 | A1* | 1/2011 | Zhuang et al. | 382/154 |

OTHER PUBLICATIONS

Quan, et al. "Ultra-fast, high-precision image analysis for localization-based super resolution microscopy." Optics Express. 18.11 (2010): 11867-11876. Print.*
Kautsky, et al. "A new wavelet-based measure of image focus." Pattern Recognition Letters. 23. (2002): 1785-1794. Print.*
Manley, et al. "Single-Particle Tracking Photoactivated Localization Microscopy for Mapping Single-Molecule Dynamics." Methods in Enzymology. 475. (2010): 109-120. Print.*
Cheezum, et al. "Quantitative Comparison of Algorithms for Tracking Single Fluorescent Particles." Biophysical Journal. 81. (2001): 2378-2388. Print.*
Ram, et al. "Improved single particle localization accuracy with dual objective multifocal plane microscopy." Optics Express. 17.8 (2009): 6881-6898. Print.*
Sillibourne, et al. "Assessing the Localization of Centrosomal Proteins by PALM/STORM Nanoscopy." Cytoskeleton. 68. (2011): 619-627. Print.*
Moller, et al. "Adaptive Segmentation of Particles and Cells for Fluorescent Microscope Imaging." VISIGRAPP 2010, CCIS. 229. (2011): 154-169. Print.*
Moreno-Hernandez, et al. "Three-dimensional particle position using continuous wavelet and circle Hough transforms." Opt. Eng.. 50.5 (2011): 1-11. Print.*

Henriques, et al. "QuickPALM: 3D real-time photoactivation nanoscopy image processing in ImageJ." Nature Methods. 7.5 (2010): 339-340. Print.*
Olivo-Marin, Jean-Cristophe "Extraction of spots in biological images using multiscale products." Pattern Recognition. 35. (2002): 1989-1996. Print.*
Quan et al. "Ultra-fast, high-precision image analysis for localization-based super resolution microscopy." Optics Express. 18.11 (2010): 11867-11876. Print.*
David S.C. Biggs: "3D Deconvolution Microscopy" in: "Current Protocols in Cytometry", Apr. 1, 2010, John Wiley & Sons, Inc., Hoboken, NJ, USA, XP55030709, ISBN: 978-0-47-114295-9 pp. 1-20.
Extended European Search Report on EP 12 16 6450.2 dated Jul. 2, 2012.
I. Izeddin et al., "Super-Resolution Dynamic Imaging of Dendritic Spines Using a Low-Affinity Photoconvertible Actin Probe," PLOS ONE, vol. 6, No. 1, Jan. 17, 2011, pp. 1-14, XP55030595, DOI: 10.1371/journal.pone.0015611.
I. Izeddin, J. Boulanger, V. Racine, C.G. Specht, A. Kechkar, D. Nair, A. Triller, D. Choquet, M. Dahan, and J.B. Sibarita, "Wavelet analysis for single molecule localization microscopy," Opt. Express 20, 2081-2095 (2012) http://www.opticsinfobase.org/oe/abstract.cfm?URI=oe-20-3-2081.
Ignacio Izeddin, Mohamed El Beheiry, Jordi Andilla, Daniel Ciepielewski, Xavier Darzacq, and Maxime Dahan, "PSF shaping using adaptive optics for three-dimensional single-molecule super-resolution imaging and tracking," Opt. Express 20, 4957-4967 (2012) http://www.opticsinfobase.org/oe/abstract.cfm?URI=oe-20-5-4957.
L. Vincent et al., "Watersheds in Digital Spaces: An Efficient Algorithm Based on Immersion Simulations," IEEE Trans. on Pattern Analysis and Machine Intelligence, vol. 13, No. 6, pp. 583-598, Jun. 1991.
S. Wolter et al., "Follow-up to paper by S. Wolter, M. Schuttpelz, M. Tscherepanow, S. van de Linde, M. Heilemann and M. Sauer, entitled Real-Time Computation of Subdiffraction-Resolution Fluorescence Images," Journal of Microscopy, vol. 245, Issue 1, p. 109, Jan. 2012, Article first published online: Oct. 25, 2011.
S. Wolter et al., "Real-time computation of subdiffraction-resolution fluorescence images," Journal of Microscopy, vol. 237, Issue 1, p. 1201322, Jan. 2010, Article first published online: Aug. 26, 2009.
European Examination Report on PCT/EP2013/050706 dated Sep. 22, 2914.
International Preliminary Report on Patentability on PCT/EP2013/050706 dated Nov. 13, 2014.

* cited by examiner

METHOD AND APPARATUS FOR SINGLE-PARTICLE LOCALIZATION USING WAVELET ANALYSIS

CROSS-REFERENCE TO RELATED APPLICATION

This application claims the benefit of European Application No. 12166450.2, filed on May 2, 2012, which application is incorporated herein by reference in its entirety.

BACKGROUND

The field of optical microscopy for biological applications has taken a qualitative leap forward with the technical advances leading to the detection of single particles. In recent years, single particle experiments have become routine in many laboratories using imaging techniques in biology and biophysics, providing new insights into a multitude of biological processes. In most cases, the first step for a quantitative analysis of single particle experiments is the determination of the position of the particle with sub-pixel accuracy in the nanometer range, well below the diffraction limit of light microscopy. For instance, the precise position of fluorescently labeled proteins in consecutive time-lapse images can be used to determine the diffusion properties of specific membrane proteins or to unravel the stepping mechanisms of molecular motors.

In recent years, several super-resolution optical microscopy techniques have been developed that surpass the diffraction limit of light in optical systems (typically about 250 nm). Among these are (fluorescence) photoactivation localization microscopy ((F)PALM), stochastic optical reconstruction microscopy (STORM), and (GSD) ground state depletion microscopy. These techniques are based on the sequential photo-switching of sparse subsets of single fluorophores. They exploit the ability to accurately determine the center of the point spread function (PSF) created by each single point emitter; ultimately, the resolution of the image is determined by the achieved particle localization accuracy. These techniques have become widespread due to their affordability and relatively simple implementation on a conventional total internal reflection fluorescence (TIRF) microscope.

Generally, stochastic optical reconstruction includes three steps: (i) the acquisition of tens of thousands of images of single particles from the sample; (ii) the precise localization of up to a million isolated single emitters; and (iii) the visualization of the super-resolved image reconstructed from the position of detected individual particles. The sequential nature of these steps, together with the high acquisition frame rate and the heaviness of the processing step, usually prevent the user from viewing super-resolution images during image acquisition. As a result, for the routine user it is not possible to access the data prior to post-processing, leading to a tremendous loss of time since the overall acquisition pipeline has to be fragmented.

FIG. 1 illustrates a typical procedure 100 for recording and reconstructing a super-resolution image with a stochastic optical reconstruction technique like PALM microscopy. The procedure 100 involves acquiring the images with a fluorescence microscope (not shown), then post-processing the acquired images according to the following steps. In step 102, a short pulse of visible light activates a subset of fluorophores widely separated far enough to individually resolve each PSF. In step 104, a second laser with a different wavelength is used to excite the active fluorophores until their (irreversible) photobleaching while one or several images 112 are recorded. Steps 102 and 104 are repeated sequentially to activate, then irreversibly photobleach different subsets of fluorophores until the density of imaged fluorophores is high enough for a complete reproduction of the structure of interest (typically a few thousand frames). Once image acquisition is complete, post-processing occurs, starting with the detection of the imaged fluorophores in step 106 on a frame-by-frame basis. Once a possible fluorophore is detected in a particular frame, its location is determined by fitting a Gaussian with a profile similar to the PSF in step 108. Step 108 is repeated for each frame of the acquired data. The reconstructed image in step 110 is obtained by superposition of all the localizations to form a super-resolution image 116. As understood by those of skill in the art, one or more processors and/or processing units may perform steps 106, 108, and 110.

The standard mathematical model used for PSF fitting is a two-dimensional Gaussian function, due to its good performance in terms of localization. Normally acquisition steps 102 and 104 take minutes, while processing steps 106, 108, and 110 may take up to several hours of computation when Gaussian fitting is carried out, since it requires an iterative minimization step, typically a maximum-likelihood estimation (MLE) or non-linear least squares (NLLS). This makes it virtually impossible to quickly evaluate the results obtained in the microscope right after acquisition, and to improve the experimental conditions on-site. Recently, a massively parallel implementation of MLE Gaussian fitting has been proposed. This solution greatly reduced the computation time, but required the use of a dedicated graphics processing unit (GPU) hardware architecture.

SUMMARY

Embodiments of the present disclosure include an apparatus, a corresponding method, and a corresponding non-transitory computer program product for estimating a position of one or more particles (e.g., cells, molecules, and/or particles tagged with fluorescent markers) in a three-dimensional (3D) space. In at least one case, the apparatus includes an imaging system, such as an astigmatic imaging system, with a point-spread function (PSF) that is asymmetric with respect to the imaging system's optical axis. The apparatus may also include a detector that is in optical communication with the imaging system and configured to detect an image of a plane in the 3D space. A memory operably coupled to the detector is configured to store a representation of the image. The apparatus also includes a processor, which may be operably coupled to the memory and/or the detector. In at least some embodiments, the processor includes a graphics processing unit (GPU) that is configured to perform one ore more of the steps described below.

In at least some embodiments, the processor is configured to locate the particle(s) by performing a series of steps, which may be encoded as instructions stored in a non-transitory computer program product. The processor receives the (representation of the) image and performs a wavelet decomposition of the image form a wavelet map of the image. The processor may be configured to perform the wavelet decomposition using the à trous wavelet decomposition technique or any other suitable wavelet decomposition technique.

The processor segments the resulting wavelet map into at least one region having intensity values above a predetermined threshold, e.g., by performing a watershed calculation on at least part of the wavelet map. In some cases, segmenting the wavelet map may include (i) determining a background noise level associated with the wavelet map; (ii) estimating a standard deviation associated with the background noise level; and (iii) selecting the predetermined threshold based on the standard deviation. For instance, the processor may select the predetermined threshold to be about 0.5 times to about 2.0 times the standard deviation.

In response to the segmentation of the wavelet map, the processor estimates the location of the segmented region's centroid, or center of mass. The centroid's location corresponds to the particle's position in a first dimension and a second dimension in the 3D space. For example, the centroid's location may represent the particle's transverse (e.g., x, y) position within the plane of the 3D space imaged by the imaging system. In some cases, the processor may estimate the location of the particle in the first dimension and the second dimension to a precision of about 1 nm to about 5 nm.

In some embodiments, the processor is configured to decompose the image, segment the wavelet map, and/or estimate the centroid while the imaging system acquires another image of the 3D space. For instance, the processor may be configured to perform these steps in real-time during image acquisition at frame rates of 50 frames per second, 75 frames per second, 100 frames per second, or more.

The processor also determines a fit of the imaging system's PSF to the region of the segmented wavelet map. For instance, if the imaging system is astigmatic, the processor non-isotropic Gaussian representing the imaging system's PSF to the segmented region. The processor may use the centroid as an estimate of the fitted PSF's center of mass.

The processor estimates the particle's position in a third dimension of the 3D space from the fit. In other words, the processor may use the fit to determine the plane's axial (z) position with respect to the imaging system's focal plane and use the plane's axial position to estimate the particle's axial position. When used with an astigmatic imaging system, the processor may estimate the axial position from the eccentricity and orientation of the ellipse fitted to the segmented region. It may do this with a precision of about 10 nm to about 50 nm.

Some embodiments also include a light source, such as a laser, to excite fluorescent emission by the particle(s). The light source emits an excitation beam whose intensity and/or wavelength can be tuned using known techniques. In these embodiments, the processor may be further configured to perform an analysis of the image and to adjust the excitation beam's intensity and/or wavelength based on the analysis of the image. The processor may also be configured to adjust at least one of a focus, a field of view, a frame size, a frame rate, and an integration time of the imaging system based on the analysis of the image.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

The accompanying drawings, which are incorporated in and constitute a part of this specification, illustrate embodiments of the disclosed technology and together with the description serve to explain principles of the disclosed technology.

DETAILED DESCRIPTION

Wavelet segmentation for particle detection and centroid localization addresses limitations caused by time-consuming data analysis. The inventive apparatus and techniques can be used for single-particle imaging, super-resolution imaging, particle tracking, and/or manipulating fluorescent particles, including but not limited to biological cells, molecules (e.g., fluorescent proteins), organic fluorophores, quantum dots, carbon nanotubes, diamond, metal or dielectric beads, and particles tagged with fluorophores. There are at least two advantages of this wavelet approach: its processing time, which is more than one order of magnitude faster than that involving two-dimensional (2D) Gaussian fitting, and its very good localization accuracy, which can be on the order of nanometers. In addition, the 2D wavelet localization can be used with additional fitting techniques to provide real-time or near real-time localization in three dimensions (3D).

Single-Molecule, Wavelet-Based Localization Microscopy

Figure 1:
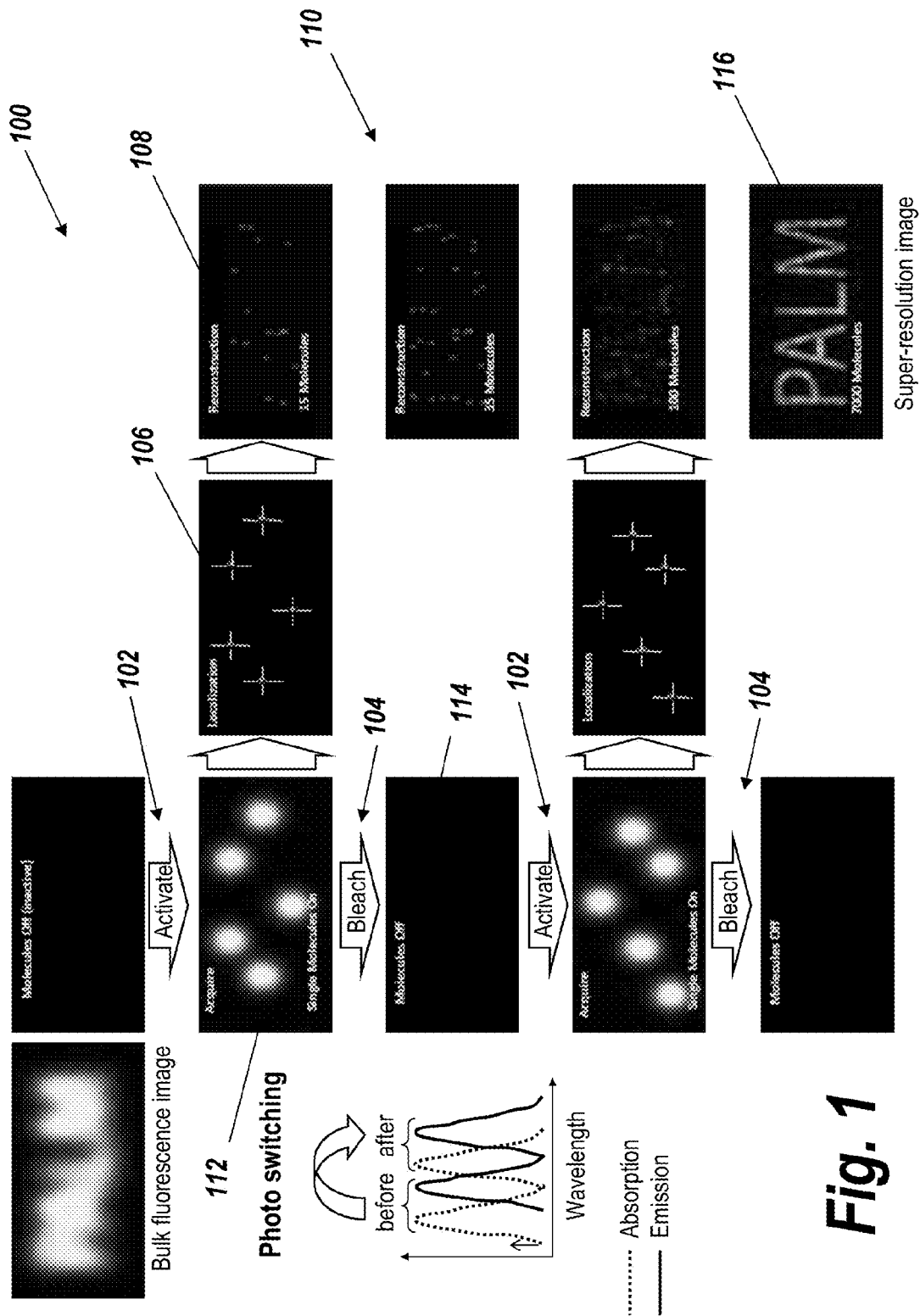
FIG. 1 illustrates acquisition and processing techniques for forming a super-resolution image based on the localization of fluorescent particles.
Figure 2A:
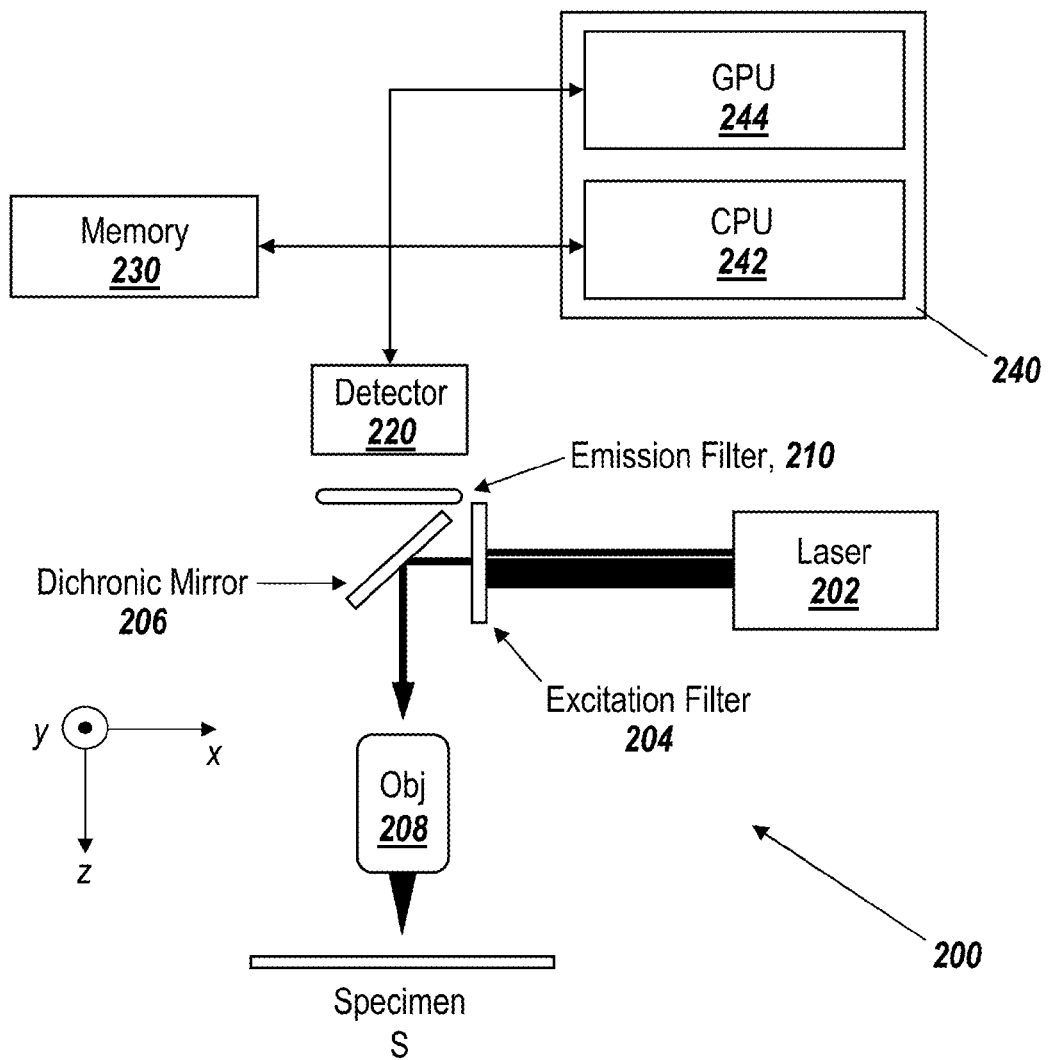
FIG. 2A is a schematic diagram of a fluorescence microscope configured to perform wavelet-based single particle localization for super-resolution imaging in both two dimensions and three dimensions.

FIG. 2A shows a fluorescence microscope 200 configured to perform both 2D and 3D single-particle localization for super-resolution imaging. Although the FIG. 2A shows a fluorescence microscope, those of skill in the art will readily appreciate that the wavelet-based techniques disclosed herein are compatible with and can be extended to any suitable imaging system. For instance, wavelet-based particle localization can also be used with any suitable fluorescence microscope, including wide-field microscopes, confocal microscopes, multi-photon fluorescence microscopes, and total-internal-reflection fluorescence (TIRF) microscopes.

The microscope 200 includes a light source 202, such as a laser, that emits light towards an excitation filter 204, such as an acousto-optic tunable filter (AOTF), which transmits light at the excitation wavelength and absorbs, reflects, or diffracts light at other wavelengths. Those of skill in the art will readily appreciate that the excitation filter 204 may be tunable and that the light source 202 itself may be a tunable laser or source capable of emitting narrowband radiation at different excitation wavelengths.

The narrowband excitation radiation reflects off of a dichroic mirror 206 towards an objective lens 208, which focuses the excitation radiation on the surface of a sample S or to a point within the sample 2. As understood by those of skill in the art, the objective lens 208 may include one or more lens elements and prismatic elements, each of which may be curved or otherwise shape to produce a beam with a predetermined point spread function (PSF). The PSF represents the shape of the blur spot produced by the focused beam. For a perfect lens, the PSF is a circle whose radius varies a function of the distance from the focal plane.

Figure 2B:
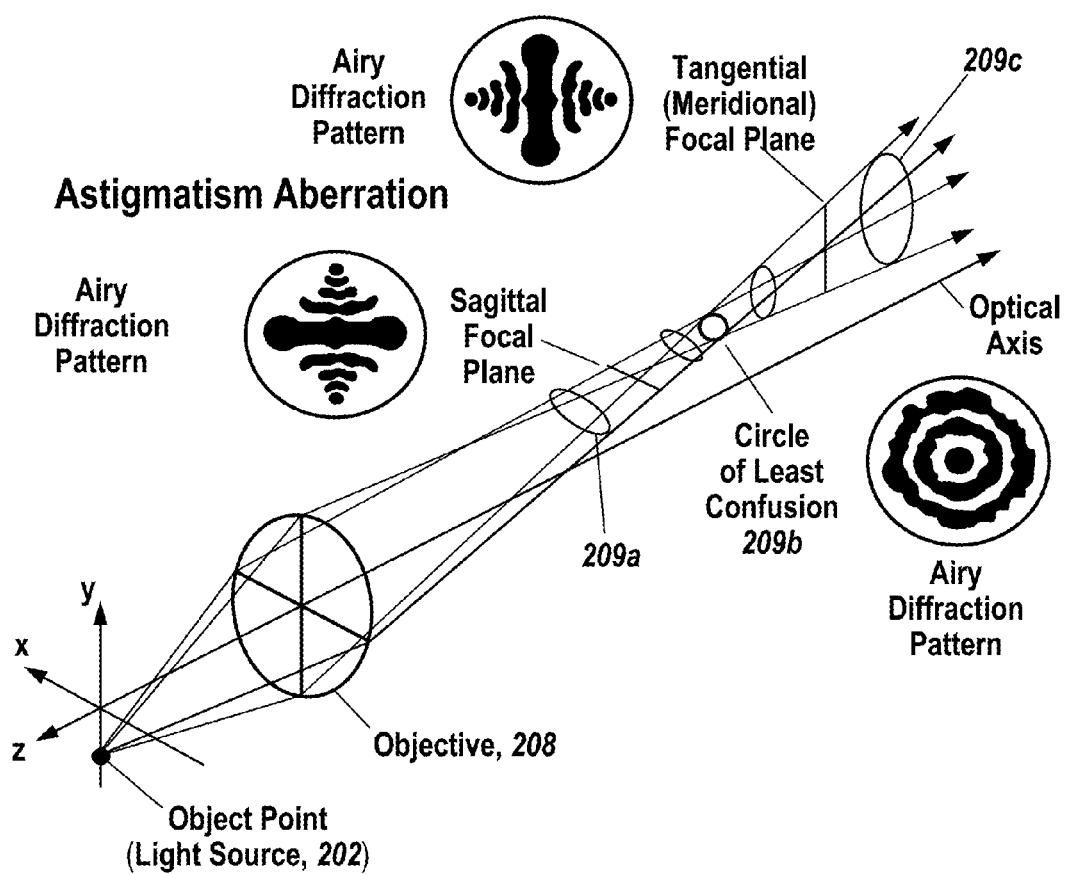
FIG. 2B illustrates an astigmatic objective whose point spread function (PSF) is asymmetric with respect to the optical axis (z dimension).

FIG. 2B shows that, unlike a perfect lens, the objective lens 208 has a PSF that is asymmetric along the objective lens's optical axis (the z axis in the coordinate system shown in FIGS. 2A and 2B). In other words, the PSF changes shape and/or orientation (as opposed to simply changing scale) as a function of distance from the objective lens's focal plane. For instance, the objective lens 208 may include a lens element or phase mask that introduces a slight astigmatism, as shown in FIG. 2B. When the objective lens 208 is astigmatic, the PSF may appear as an ellipse 209a whose semi-major axis is aligned with the x axis on one side of the focal plane, as a circle 209b at the nominal focal plane, and as another ellipse 209c whose semi-major axis is aligned with the y axis on the other side of the focal plane. Alternatively, the objective lens 208 may have a PSF that rotates as a function of position along the z axis. The PSF's asymmetry with respect to the z axis can be used to localize the particle's location in the z dimension as described below. The PSF can be calculated beforehand or determined experimentally, e.g., by imaging a known specimen and using the result to calibrate the microscope 200.

Fluorescent particles (fluophores) in the specimen S absorb excitation light and emit fluorescent radiation at an emission wavelength that is different than the excitation wavelength. The objective lens 208 images the fluorescent radiation via the dichroic mirror 206 and an emission filter 210 onto a detector 220, such as an electron-multiplying charge-coupled device (EM-CCD), a Geiger-mode avalanche photodiode array, or any other suitable detector array. Like the excitation filter 204, the emission filter 210 transmits light at the emission wavelength and absorbs or reflects light at other wavelengths to reduce blooming, noise, and other undesired effects at the detector 220.

The detector 220 transduces the incident light into a detectable electrical signal, such as a current or voltage, whose amplitude represents the image of the specimen S projected by the objective lens 208. The detector 220 is coupled to a memory 230, which stores a representation of the image, and a processor 240, which processes the image in real-time, near real-time, or off-line (e.g., in post-processing) to localize one or more particles in the specimen S. In some embodiments, the processor 240 includes at least one central processing unit (CPU) 242 and at least one graphics processing unit (GPU) 244. The CPU 242 and the GPU 244 can perform different tasks associated with wavelet-based localization to decrease computation time, e.g., for real-time or near real-time particle localization.

This hybrid CPU 242/GPU 244 architecture enables real-time analysis at image acquisition rates of 50 frames per second or higher. Since wavelet decomposition is very similar to a convolution, each pixel in the image can be processed independently of the other pixels in the image. The local nature of wavelet decomposition suits parallel pixel by pixel processing on the GPU 244. Practically, computation time with a hybrid CPU/GPU processor 240 can be about seven times faster for an image of 500,000 molecules than a CPU-only implementation.

2D and 3D Wavelet-Based Localization

Figure 2C:
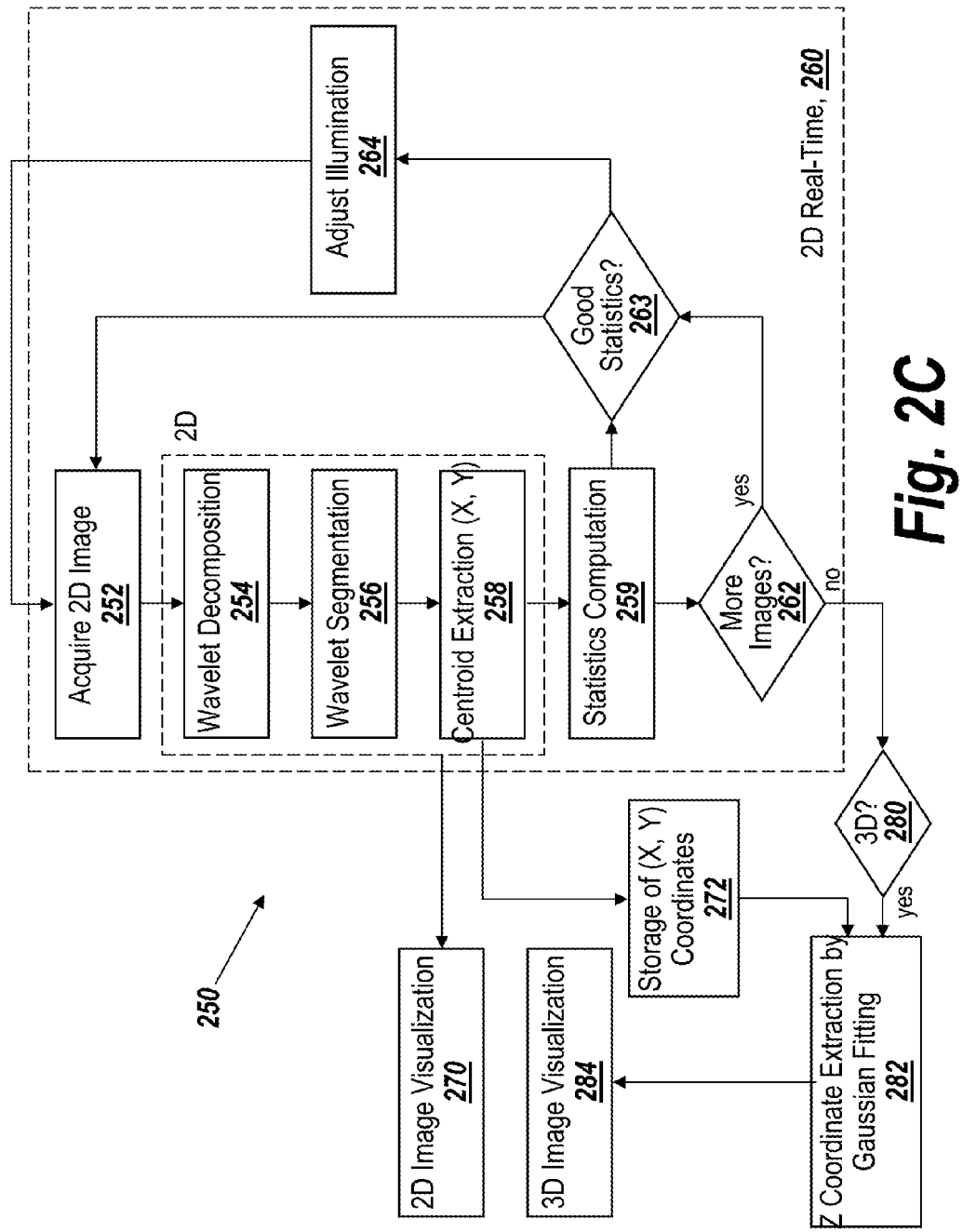
FIG. 2C is a flow diagram that illustrates two-dimensional and three-dimensional wavelet-based particle localization.

FIG. 2C is a flow diagram that illustrates both a 3D wavelet-based image segmentation and particle localization process 250 and a 2D (real-time) wavelet-based single particle localization process 260 that forms part of the 3D process 250. Both the processes 250 and 260 begin with acquisition (step 252) of at least one 2D image with zero, one, or more than one fluorescent particle, e.g., using the microscope 200 shown in FIG. 2A or any other suitable imaging system. (If no particle appears in the image, then no particle is localized.) Wavelet filtering removes image noise and enables hard thresholding and object segmentation. A watershed algorithm is applied after labeling to allow closely fused particles to be separated and localized in 2D using centroid segmentation. Fitting to the PSF shape is used to retrieve the axial position of the localized particle, yielding the particle's 3D position.

These processes 250, 260 enable a user to view a super-resolved image during image acquisition. They also offer the possibility of optimizing the acquisition process by controlling the acquisition and localization parameters in real-time as described in greater detail below. The localization processes 250, 260 allow precise retrieval of the spatial coordinates of each particle, in either two (2D) or three (3D) dimensions, with nanometer-scale resolution (e.g., within 1 nm, 2 nm, 3 nm, 4 nm, 5 nm, or 10 nm, or any other value between a few nanometers and about 50 nm) depending on the SNR of each molecule image. Unlike Gaussian PSF fitting, which can be too time consuming for real-time reconstruction at high acquisition frame rates (e.g., rates of 50 frames per second, 100 frames per second, or higher), wavelet-based localization can be used to for real-time processing at frame rates of 50 frames per second or more.

2D Particle Localization

In step 254, a processor (e.g., the hybrid CPU/GPU processor 240 shown in FIG. 2A) decomposes the 2D image into wavelet maps using an undecimated wavelet transform called "à trous" using a B-Spline of third order. (Other wavelet transforms may work as well.) The à trous wavelet transform is well-known and described in greater detail below. The processor can execute the à trous wavelet decomposition quickly and accurately to detect one or more isotropic spots. This decomposition yields a first wavelet map (or first wavelet plane) that contains the high frequencies of the source image (e.g., as shown in the second column of FIG. 4, described below), which is where most of the noise is present. It also yields a second wavelet map (or second wavelet plane) that contains the structures with sizes close to the diffraction limit (e.g., as shown in the third column of FIG. 4). This second wavelet map is well suited for single particle localization. Higher wavelet maps may contain coarser image details and lower spatial frequencies.

As part of step 254, the processor extracts the second wavelet plane by applying a fixed threshold, whose value ranges between about 0.1 times and about 10 times (e.g., about 0.5 times to about 2.0 times) the standard deviation of a background noise level associated with the 2D image. For instance, the processor may begin with a threshold equal to the standard deviation and adjust the threshold based on image quality and/or in response to user input. It may also determine this background noise level, which may be the maximum noise level, by estimating the background Gaussian noise from the first wavelet map. If the specific signal of single particles is sparse, as desired for single particle based super-resolution, the standard deviation of the source image is a good estimate of the noise level used for thresholding. The thresholds used for the wavelet segmentation of the images shown in the fourth column of FIG. 4 were set to 0.5 times the standard deviation of the noisiest image.

Single particle based super-resolution imaging may benefit from using a large number of detected particles to (re)construct an image. For some biological applications, notably live-cell dynamics, high imaging rates are required and thus images with high density of fluorescent single particles are acquired. This may result in inaccurate particle localization when multiple PSFs from different particles overlap (see the upper left asterisk in the middle and bottom images of the first column in FIG. 4).

In step 256, the processor splits or segments the second wavelet map into regions with one particle each. The processor may segment the second wavelet map by applying a watershed algorithm. Applying the watershed algorithm may involve determining that the regions representing particles have intensity values above a predetermined threshold and that the regions representing the absence of particles have intensity values below a predetermined threshold. The processor may also remove regions below a certain size (e.g., less than four pixels) to avoid possible remaining localizations due to noise.

In step 258, the processor estimates the location of the centroid, or center of mass, for each region that represents a particle. Because the image is 2D, the centroid represents a particle's transverse coordinates (e.g., its x and y coordinates) in the plane of the 3D volume represented by the image. Depending on the image's SNR, the processor may be able to locate the centroid with an accuracy of better than 10 nm, 5 nm, 4 nm, 3 nm, 2 nm, or even 1 nm. The processor may use the results of this centroid extraction to create a 2D super-resolution image of the particle in step 270. It may also store the particle's transverse coordinates in memory (step 272) for further processing, including 3D image visualization (step 284) as described below.

In step 259, the processor performs a statistics computation or analysis based on the image (or image characteristics) derived through wavelet decomposition, wavelet segmentation, and/or centroid extraction. For instance, the processor may determine the number, intensity, and spatial distribution of particles in the image. In step 262, the processor determines whether or not it has acquired all the desired 2D images. If there are more images to be acquired, the processor checks in step 263 to see whether the image statistics determined in step 259 are acceptable. If not, the processor may adjust the intensity of the beam used to excite fluorescent emission from the particle(s) in step 264. It may also cause the imaging system to focus on another plane within the 3D volume.

3D Particle Localization 3D localization involves exploitation of a priori knowledge of the imaging system's PSF to find a particle's axial position, or position in a third dimension in a 3D space (e.g., the z dimension). PSF engineering, e.g., using an astigmatic lens, allows the retrieval of the axial position. Practically, this information is usually computed by applying a Gaussian fitting around the particle, using sophisticated methods, like Maximum-Likelihood Estimation (MLE) or Non-Linear Least Squares (NLLS). Despite the reliability of MLE and NLLS in terms of localization accuracy, the time required to reconstruct the final image remains an obstacle to data production in routine. Other methods were proposed like Quick-PALM (classical Högbom 'CLEAN' method) or LivePALM (fluoroBancroft algorithm). These techniques are very efficient in terms of computation time but may be limited to off-line processing (post-processing).

If the processor indicates or receives an indication in step 262 that all of the desired 2D images have been acquired, it determines whether or not to create a 3D image in step 280. If a 3D image is desired, the processor locates the axial (z) position of one or more of the previously localized particles (step 282), e.g., with an accuracy of 50 nm, 40 nm, 25 nm, 10 nm, 5 nm, or better. In certain embodiments, the processor's GPU performs this 3D localization by fitting a function based on the imaging system's asymmetric PSF around each particle's transverse position (centroid). The function parameters as a function of the z dimension may be determined through calibration of the imaging system. The axial coordinate of a localized particle can be retrieved by performing a local fitting of the raw data around the coordinates (e.g., the centroid) already computed by the wavelet segmentation process.

If the imaging system is astigmatic, for instance, the GPU may compute a fit based on a PSF that is elliptically shaped with an eccentricity orientation that change along the optical axis (the axial or z dimension). For instance, the GPU may fit a non-isotropic Gaussian to a 9 pixel×9 pixel area using nonlinear least squares in order to compute the ellipse parameters (e.g., the sizes and orientations of the ellipse's major and minor axes) used for determining the particle's axial coordinate. The more eccentric the fitted ellipse, the farther the particle is from the objective lens's focal plane. The orientation of the ellipse's major axis indicates whether the particle is on the near side or the far side of the focal plane. A perfectly circular fit indicates that the particle is at the focal plane. Those of skill in the art will readily appreciate that other fitting functions and/or other PSFs are also possible.

This fitting step can be time consuming when performed in the CPU, suggesting a GPU-based implementation. Nevertheless, real-time constraints may not allow massively parallel implementation. Consequently, even a GPU-based implementation may not allow the Gaussian fitting to be performed in real time. Therefore, for real-time or near real-time particle localization, the processor may implement a two-step approach: i) compute the 2D image in real-time using wavelet segmentation (process 260); and ii) compute the fitting and 3D extraction right after the end of the image acquisition (step 266). GPU implementation enables computing the axial coordinates of a million particles in few minutes compared to a few tens of minutes with a CPU alone. This enables the user to access 3D information within seconds to minutes after the acquisition process, which is fast enough for practical use. The calculations are almost twenty times faster in the case of GPU versus CPU. The GPU implementation can efficiently utilize the parallel nature of 3D fitting where the PSF of each detected particles is different in a lateral plane.

"À Trou" Wavelet Implementation

Define V {i} as the coefficient map at level i and W{i} as the wavelet (or detail) coefficient map at the level i. V {i} and W {i} have the same size than the original image. W{2} is the second wavelet map, which is segmented using threshold and watershed techniques as described above. In one implementation, a trous wavelet decomposition includes the following steps:

(1) Initialize V {0} to the original image;
(2) Calculate V {1}: V {1}=convV(convH(V {1}, g{1}), g{1});
(3) Calculate V {2}: V {2}=convV(convH(V {2}, g{2}), g{2}); and
(4) Calculate W {2}: W {2}=V {1}-V{2}.

Here, g{1} refers to the low pass [H2, H1, H0, H1, H2], and g {2} refers to the low pass [H2, 0, H1, 0, H0, 0, H1, 0, H2], with H0=3/8, H1=1/4, H2=1/16. convH refers to the convolution over the columns and convV refers to the convolution over the lines.

Imaging Control Using Real-Time Localization

Figure 2D:
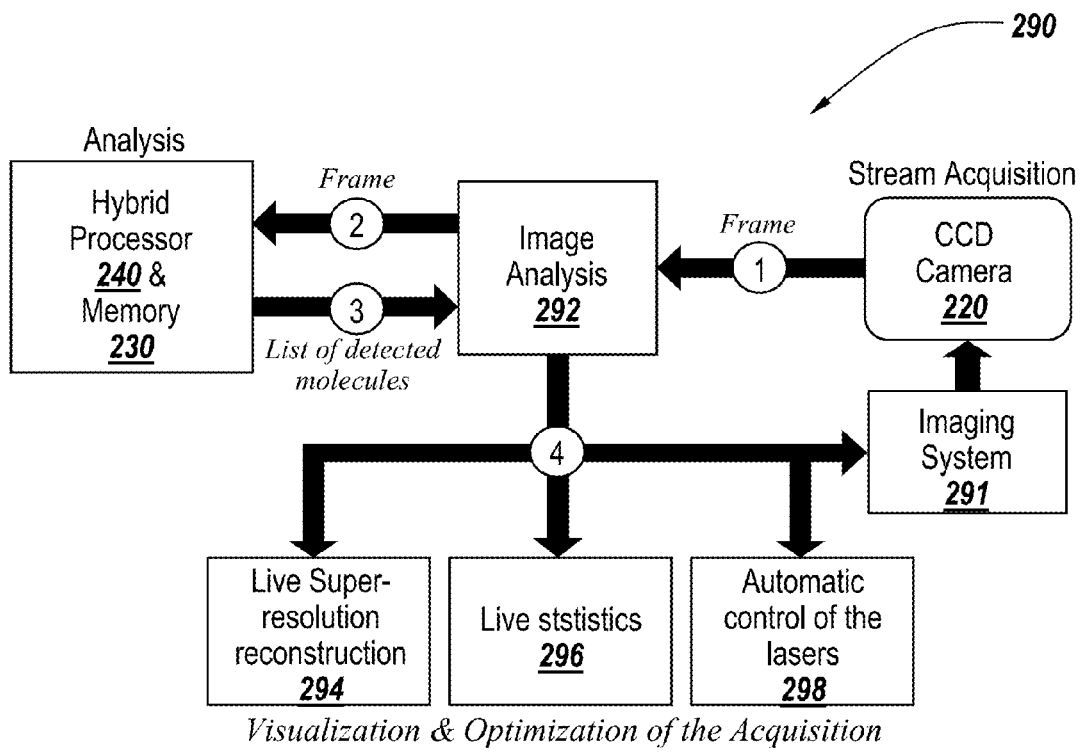
FIG. 2D illustrates a system that uses real-time and/or near real-time wavelet-based particle localization for controlling image acquisition.

FIG. 2D illustrates a system 290 for using real-time or near real-time particle localization to control image acquisition by an imaging system 291. The imaging system 291 may include one or more lenses (e.g., an objective lens 208 (FIG. 2A)) or other optical elements and/or one or more stages for changing the position of the focal plane relative to the location of the 3D space (specimen S (FIG. 2A)). The system 290 includes a CCD camera 220 to acquire images (frames) and a GPU 244 (e.g., part of a hybrid processor 240) and a memory 230 to perform image analysis 292, including particle localization for super-resolution image reconstruction 294, live particle/image statistics 296, and automatic imaging system control 298.

The processor 240 may control the intensity of the source (laser) 202 used to excite the particles. For instance, the processor 240 may turn up the source's intensity so as to increase the number of particles visible in a given image. It may also turn down the source's intensity so as to decrease the number of particles visible in a given image, e.g., because too many or too few particles appear in the field of view to be localized with a given frame acquisition period. In certain embodiments, the processor 240 may also tune the emission wavelength (e.g., by tuning the laser 202 or the filter 204). The processor 240 may do this so as to excite different fluorophores or to increase or decrease the number of excited fluorophores.

The processor 240 may also move, expand, shrink, or otherwise control the imaging system's field of view for real-time regulation of the particle density per frame, possibly to achieve an optimal density. It may do this by changing the imaging system's focal plane or field of view. Alternatively, or in addition, the processor 240 may adjust or control the integration time, frame rate, and/or frame size of the CCD camera 220.

2D Wavelet Segmentation with Simulated Images

Simulations of isolated single point emitters illustrate the speed, reliability, and accuracy of the detection and position determination of wavelet segmentation and centroid determination.

Simulation of Realistic Single Particle Images

Single particles images were simulated using 2D isotropic Gaussians, of maximum intensity $I_0$, standard deviation a, and intensity offset B, sampled in a discrete space of pixel size D. σ and D refer to the objective resolution and the CCD camera pixel size in the object space, respectively. In this case, σ=1 and D=100 nm for simulating ideal sampling for high NA objective. $2\pi\sigma I_0$ refers to the number of collected photons $N_P$ per single particle. The offset $I_B$ value is 1000 grey levels and $I_0$ intensities ranged from 100 to 1000 grey levels, compatible with the number of photons emitted by conventional genetic fluorescent proteins and organic single particle dyes used in super-resolution microscopy. The images are corrupted by a mixture of Poisson (photon) and Gaussian (electronic) noise. At each pixel p, the noise model for the intensities $I_P$ of the simulated images is the sum of a Poisson noise of rate $\mu_p$ coming from the limited number $N_P$ of photons and a Gaussian noise $B_P$ of mean $I_B$ and variance $\sigma_B$ summarizing the electronic noises. A gain g represents the ratio of gray levels per photo-electrons in the image collected by the CCD. Finally, the intensity can be written as $I_P = gN_P + B_P$. For each image, the SNR is defined as $$SNR = I/\sqrt{\sigma_B^2 - \sigma_I^2}$$

where I is the maximum intensity of the single particle signal, $\sigma_B^2$ is the variance of the background intensities, and $\sigma_I^2$ accounts for the photon noise, computed as the integrated signal for the single particle, proportional to the number of photons.

Figure 3:
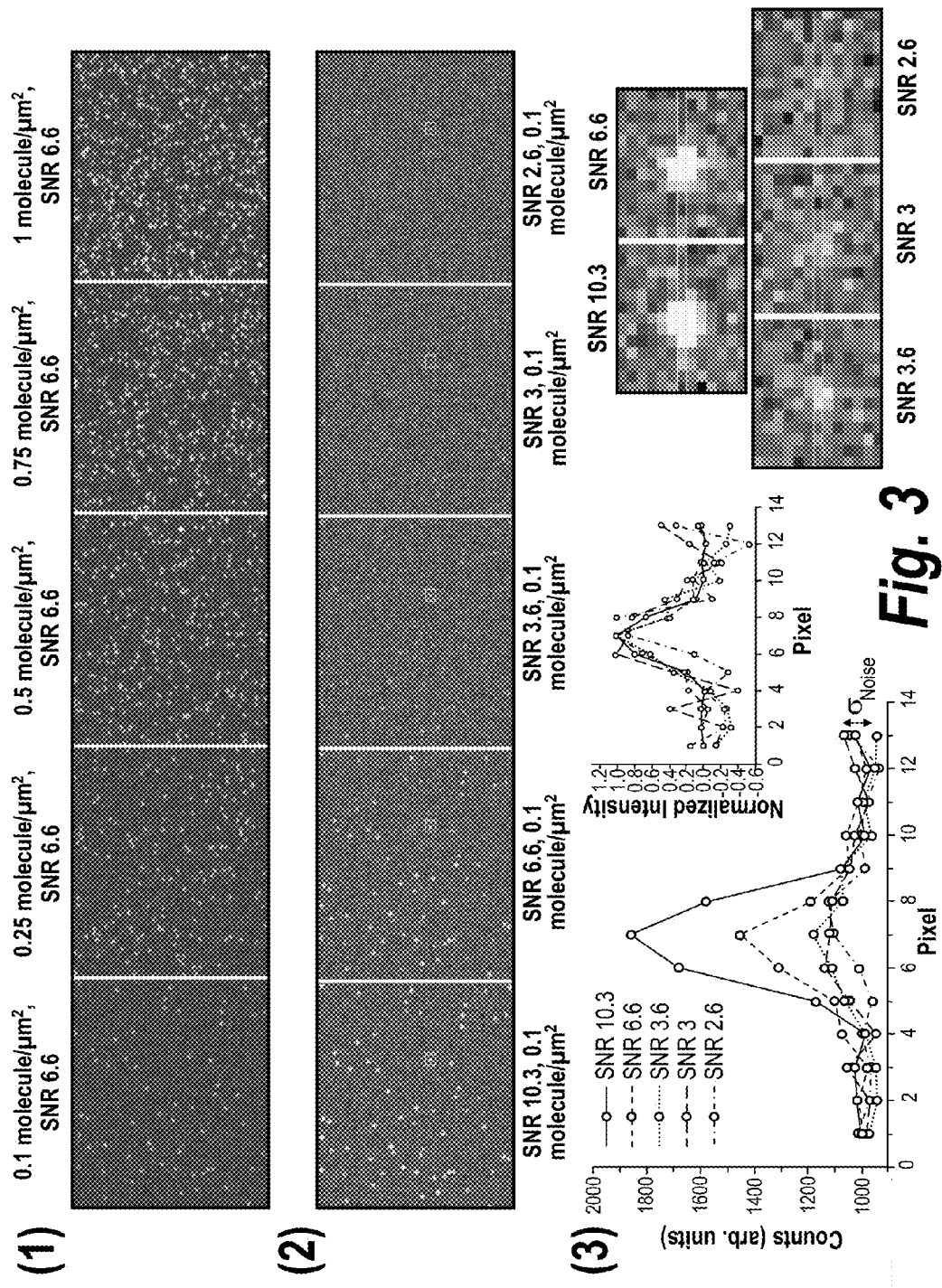
FIG. 3 shows simulated images of single particles on a 256 pixel×256 pixel matrix of 100 nm pixel size.

FIG. 3 shows simulated images of single particles on a 256 pixel×256 pixel matrix of 100 nm pixel size. Each single point is convolved with a 2D Gaussian function with variance $\sigma^2=1$ pixel (e.g., a FWHM of 250 nm), and then sampled on a 256 pixel×256 pixel matrix with a pixel size of 100 nm. The image was then corrupted with a mixture of Gaussian and Poisson noise. These simulations were performed with different SNRs and particle densities per image. SNR values ranging from 2.6 to 10.3 and particle densities from 0.1 particle/μm² to 1 particle/μm² cover the range of experimental conditions encountered in PALM and STORM imaging using fluorescent proteins or organic fluorescent dyes. For each given SNR and density, a series of 100 frames of randomly redistributed particles was generated.

In FIG. 3, examples of such synthetic data are shown for increasing particle density and decreasing SNR. Panel (1) of FIG. 3 shows examples at an SNR=7.1 and particle densities of 0.1, 0.25, 0.5, 0.75, and 1 particle/μm² (left to right). Panel (2) shows examples at a molecular density of 0.1 particle/μm² and SNRs in linear units of 10.3, 6.6, 3.6, 3, and 2.6 (from left to right). Panel (3) includes a plot (left) of intensity profile across one single particle for different SNRs, normalized in the inset, and raw images of the same data (right). Typical SNR values of the data shown in FIG. 3 are about 8, depending on the chosen fluorophore and simulated experimental conditions. Investigating performance at lower SNRs covers both fluorescent probes with lower quantum yield and single-particle tracking of photoactivatable fluorophores (spt-PALM), both of which lead to fewer detected photons in each image frame.

Figure 4:
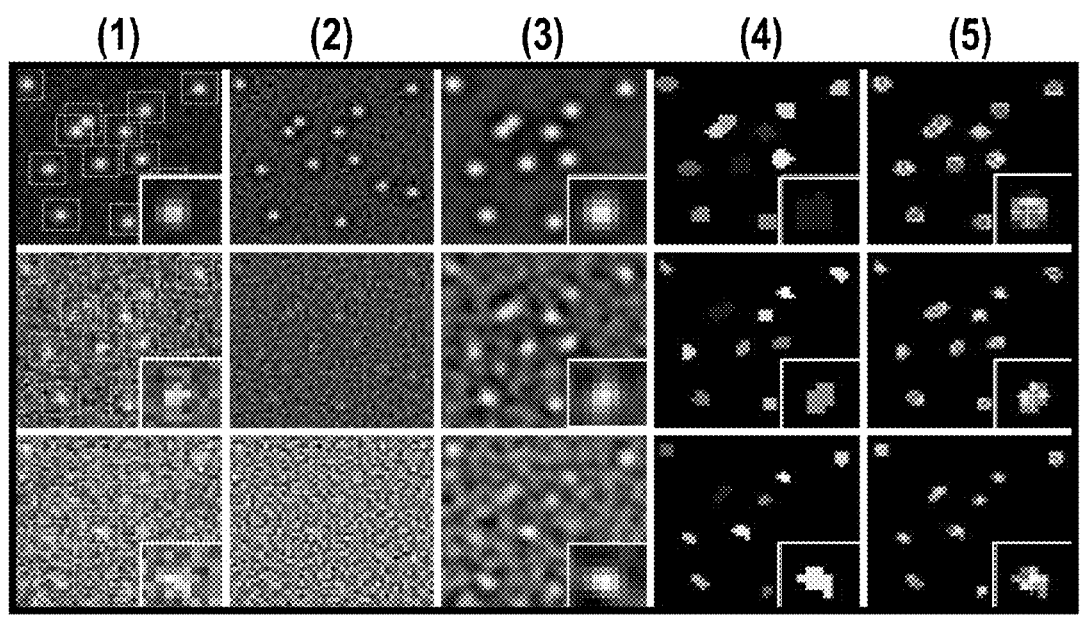
FIG. 4 illustrates wavelet segmentation using simulated data.

FIG. 4 illustrates wavelet segmentation using simulated data. Each column shows a different type of image, and each row shows a different SNR. From left to right: (1) source images with the localization of single particles in boxes; (2) the first wavelet planes associated with the source images; (3) the second wavelet planes associated with the source images; (4) the segmented images; and (5) centroid computation for each localized particle defined by the segmented images. From top to bottom: illustrations with different SNRs (10.3, 3.6, and 3, respectively), using the same segmentation threshold defined by 0.5 times the standard deviation of the noisiest image. Markers (*) illustrate false positive and false negative detection.

Wavelet Segmentation Versus Gaussian Fitting

The generated images can be used to compare the performance of the wavelet segmentation approach and a Gaussian fitting approach in terms of speed and accuracy. This comparison was performed using multiple-target tracking (MTT) as the Gaussian fitting approach. MTT is a robust technique for high-density, single-particle detection calculations with performance close to the theoretical limits. MTT uses hypothesis testing for particle detection followed by multi-parametric Gaussian fitting to estimate the subpixel position of single particles. Although MTT is capable of determining the position of overlapping PSFs and includes tracking capabilities, this comparison is limited to the detection and positioning of single PSFs, excluding deflation loops and trajectory determinations.

Both wavelet segmentation and MTT have a complexity of O(n), where n is the number of pixels in the image per frame. TABLE 1 (below) details the main steps of both methods. One difference between the two approaches is how the localization coordinates are computed. For the wavelets, a simple centroid is computed on the second wavelet map for each region. Since the number of particles and their surfaces after segmentation are limited, the complexity of the watershed can be approximated to O(n) as well. Gaussian fitting relies on a minimum of 30 iterations to extract the five parameters (x, y, σ, intensity, and offset) that describe the 2D Gaussian curve. Thus, the comparison here is based on the number of computing operations instead of their computing complexity.

TABLE 1

Gaussian and Wavelet-Based Particle Localization

| Gaussian | Wavelets |
| --- | --- |
| Filtering;<br>For each region:<br>    Loop for at least 30 times:<br>        Compute partial<br>        derivatives for five<br>        parameters (x, y, sigma,<br>        intensity, offset);<br>        Adjust the parameters to<br>        minimize the errors;<br>    End loop;<br>End for each region; | Wavelet decomposition;<br>For each region:<br>    Compute the watershed;<br>    Compute the region's centroid;<br>End for each region; |

Computation Time

One element of performing efficient imaging experiments is the ability to make decisions that might alter the experimental configuration during or right after acquisition. This may be especially useful in live cell experiments, where the effective time of the experiment under the microscope may be limited in order to maintain the physiological conditions of the samples. Long post processing times (i.e., after the actual experiment) may thus severely limit the design and possible applications of super-resolution imaging experiments, which involve the quantitative analysis of hundreds of thousands of single particle data points.

Figure 5A:
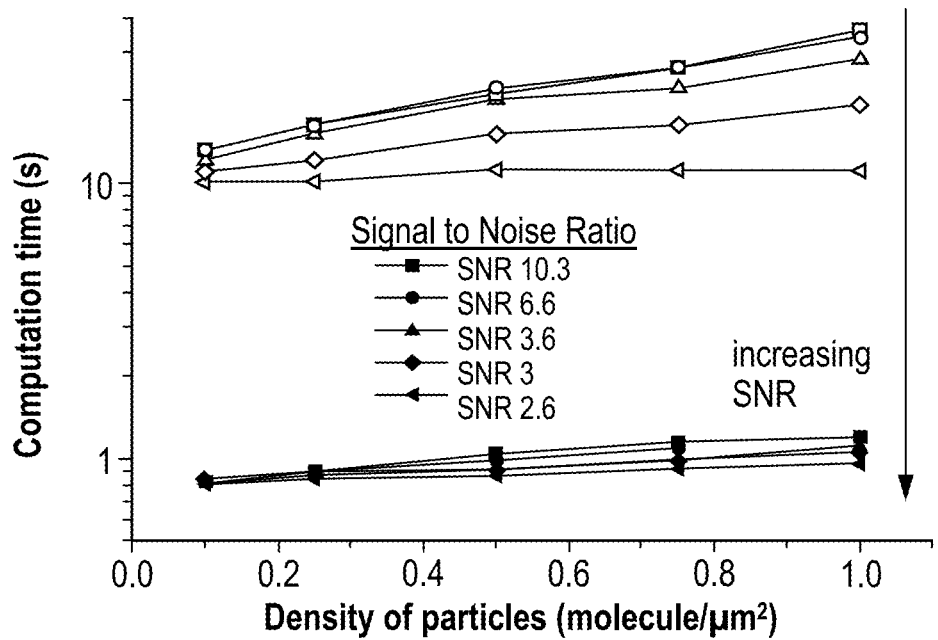
FIGS. 5A and 5B are plots of computation time for wavelet analysis and Gaussian multiple-target tracking (MTT) analysis as functions of particle density and signal-to-noise ratio (SNR), respectively.
Figure 5B:
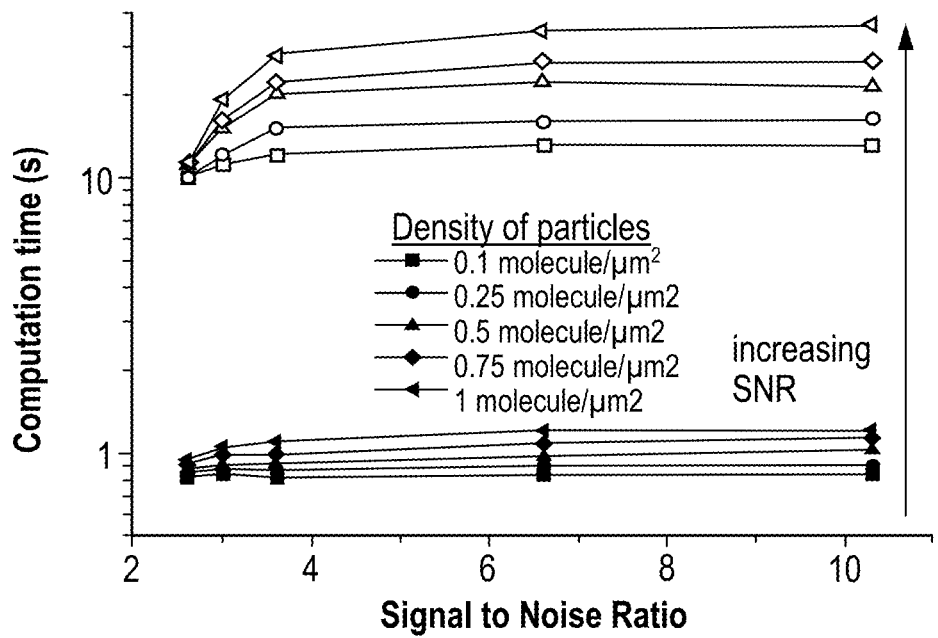
Figure 5C:
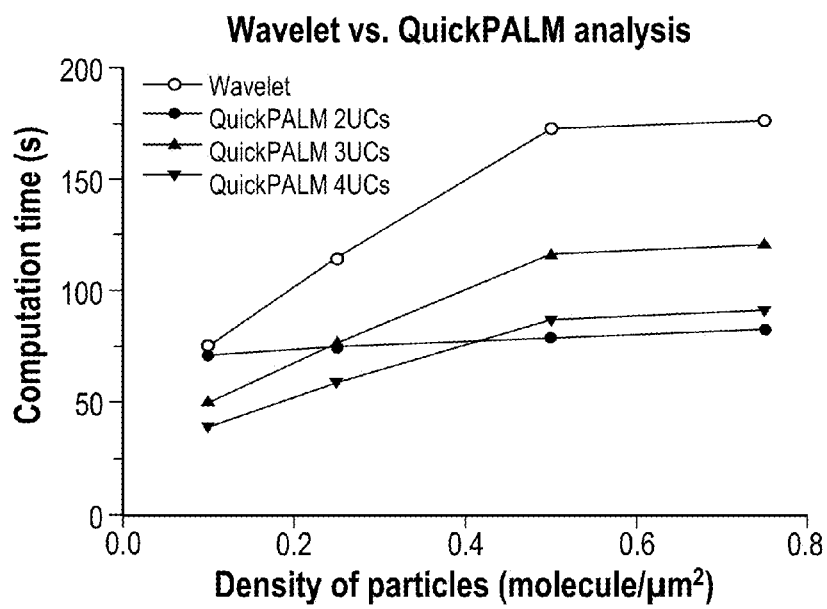
FIG. 5C is a plot of computation time for wavelet analysis and QuickPALM analysis as a function of particle density.

FIGS. 5A-5C show comparisons of calculation time for a series of 100 images at a wide range of SNRs and particle density values. These comparisons were was performed on a Dell Precision T7500 computer, with a clock speed of 2.26 GHz, 48 GB of RAM, and two quad Intel Xeon processors E5520, although only one core was used during calculation. In general, the calculation speed of the wavelet technique is more than ten times faster than MTT.

FIGS. 5A and 5B show comparisons of the computation time between the wavelet segmentation and the MTT approaches. The total time needed to detect and determine the position of a series of 100 images with simulated single particles, is represented as a function of molecular density for different SNRs (FIG. 5A), and as a function of SNR for several molecular densities (FIG. 5B). Whereas the calculation time as a function of the SNR saturates at similar values of SNR for both wavelet segmentation and MTT, the saturation level is about twenty times faster in the case of the wavelet analysis (note the logarithmic scale). On the other hand, FIG. 5A shows a linear increase of the computation time as a function of the particle density. Nevertheless, accurate experimental recordings will typically limit the particle density to the lower density levels, in order to avoid overlapping PSFs.

FIG. 5C shows a comparison between the wavelet approach and QuickPALM for a series of 4000 images on the same simulated data sets used above, with a particle density per image frame ranging from 0.1 to 0.75 particle/$\mu m^2$ and using 1 to 4 CPUs for the QuickPALM algorithm. QuickPALM uses a multithreading approach, which involves partitioning the program into many tasks that can be processed in parallel, linking its performance to the number of used processors. With QuickPALM, two to four CPU processors were used for the computation. FIG. 5C shows that wavelet segmentation is more efficient than QuickPALM for high densities (>150 particles), even with the use of four processors. For small densities (<150 particles), both wavelet segmentation and QuickPALM show similar performance, with a variability depending on the number of processors used. Unlike QuickPALM, wavelet segmentation uses only one processor even with a multiprocessor architecture. Nevertheless, since the processing of different images is completely independent in wavelet segmentation, an implementation on a multiprocessor architecture is feasible.

Figure 5D:
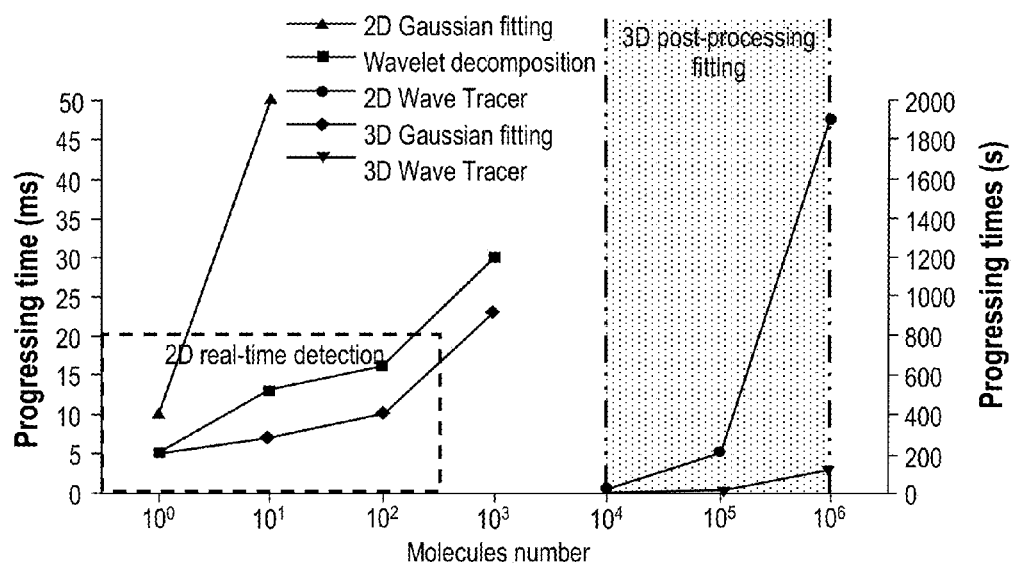
FIG. 5D is a plot of processing time versus number of particles for two-dimensional real-time detection (left) and three-dimensional post-processing fitting (right) for different particle localization techniques.

FIG. 5D is a plot of processing time versus number of particles for two-dimensional real-time detection (left) and three-dimensional post-processing fitting (right) for different particle localization techniques. 2D wavelet-based localization implemented on standard CPU processors and hybrid CPU/GPU processors ("WaveTracer") are several orders of magnitude faster than Gaussian decomposition. In fact, they are suitable for real-time image reconstruction for frame rates of about 100 frames per second (and lower) and particle densities of 100 particles per square micron. 3D wavelet-based localization is many orders of magnitude faster than 3D Gaussian fitting and can be performed in minutes or less (near real-time) even for 1,000,000 particles or more.

Localization Accuracy

The resolution of the reconstructed image depends on the accuracy in determining the position of each single fluorophore. It is hence desirable for the overall performance of any localization technique not to compromise the pointing accuracy over the calculation speed. One way to characterize the error in each particle's localization is by measuring the Euclidean distance between coordinates of simulated data and the closest coordinates in the analyzed data. The localization accuracy can then be defined as the mean value of the positioning error calculated for all the detections of each data set.

Figure 6:
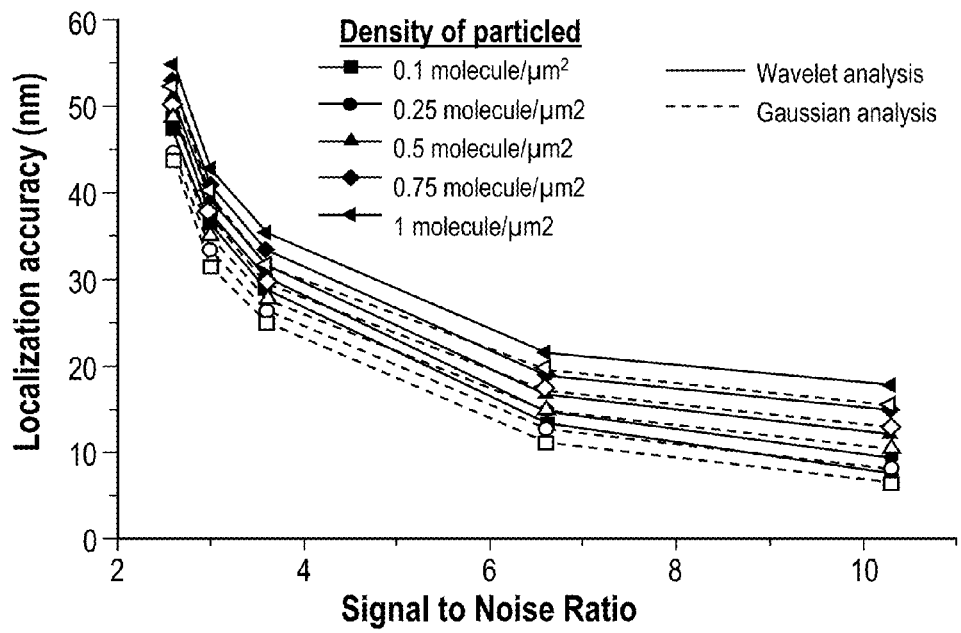
FIG. 6 is a plot of localization accuracy versus SNR for wavelet segmentation and MTT analysis at different particle densities.

FIG. 6 shows the performance of both algorithms in retrieving the position of the fluorophores as a function of the SNR. The localization accuracy was calculated as the mean value of the positioning error calculated for all the detections in each data et, and is shown as a function of the SNR for several molecular densities. As expected, the localization accuracy is inversely proportional to the SNR for high numbers of detected photons, and dominated by the background noise at low SNR. The accuracy in determining the single particle positions is comparable using both algorithms, for the entire range of SNRs and particle densities used in this study. The results obtained with the wavelet approach algorithm are summarized in TABLE 2 (below) for the different sets of simulated data with varying particle density and SNR.

False Positive and False Negative Rates

Another parameter to consider is the reliability of particle detection, or the ability to detect individual PSFs in a noisy image. For instance, if a particle present in the simulated data had no matching detection in the analyzed data set within a radius of 100 nm, it may be counted as a false negative detection. Similarly, a false positive detection can be defined as the identification of a particle in the analyzed data set that was not present in the simulated data within a radius of 100 nm.

Figure 7:
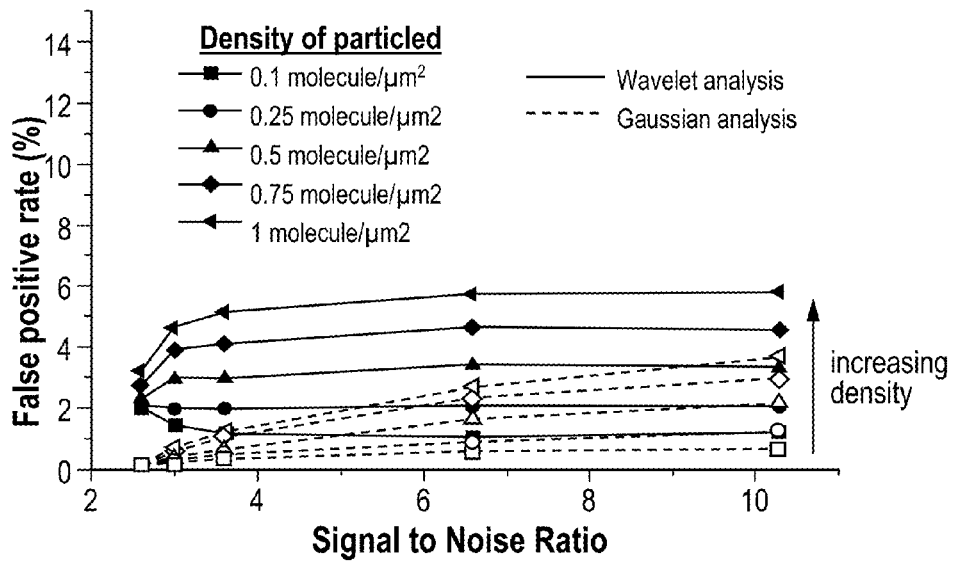
FIG. 7 is a plot of false positive detections in a radius of 100 nm around the coordinates of each simulated single particle versus SNR.
Figure 8:
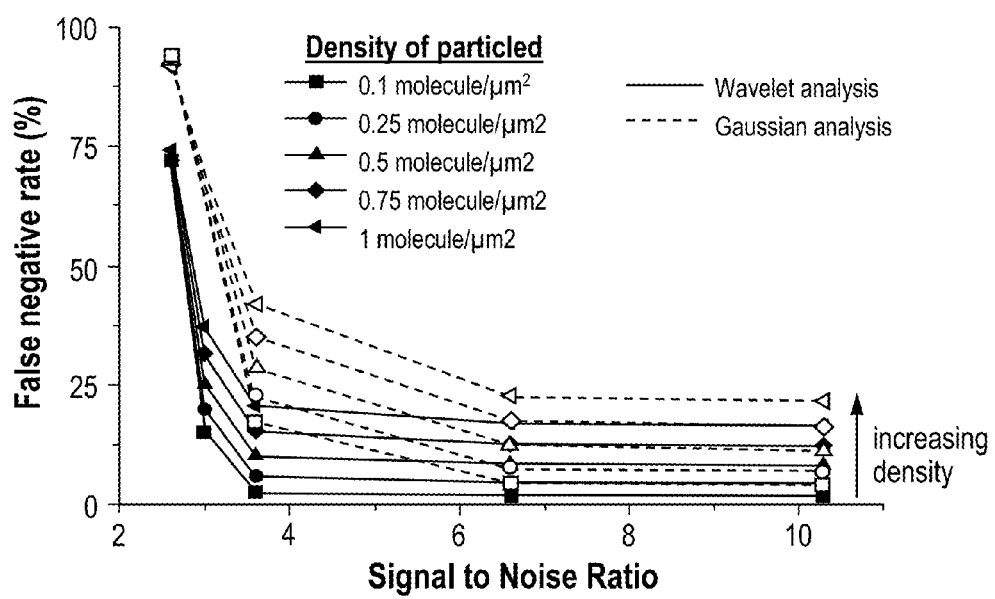
FIG. 8 is a plot of false negative detections in a radius of 100 nm around the coordinates of each simulated single particle versus SNR.

FIGS. 7 and 8 show the false positive rates and false negative rates, respectively, as a function of the SNR for the wavelet approach and MTT at different molecular densities. These plots show that the percentages of false positive and negative detections are similar for both the wavelet approach and MTT, and strongly depend on the SNR of the simulated data, except for the false positive rate performed by the wavelet analysis, which remains fairly constant at a given molecular density. Choosing a different minimum intensity threshold value may alter the false positive and negative detection rates without effectively compromising the performance in terms of calculation speed and localization accuracy. Also, noise reducing filters applied prior to particle detection and localization may improve the detection errors.

Test Pattern Simulations

Figures 9A, 9B:
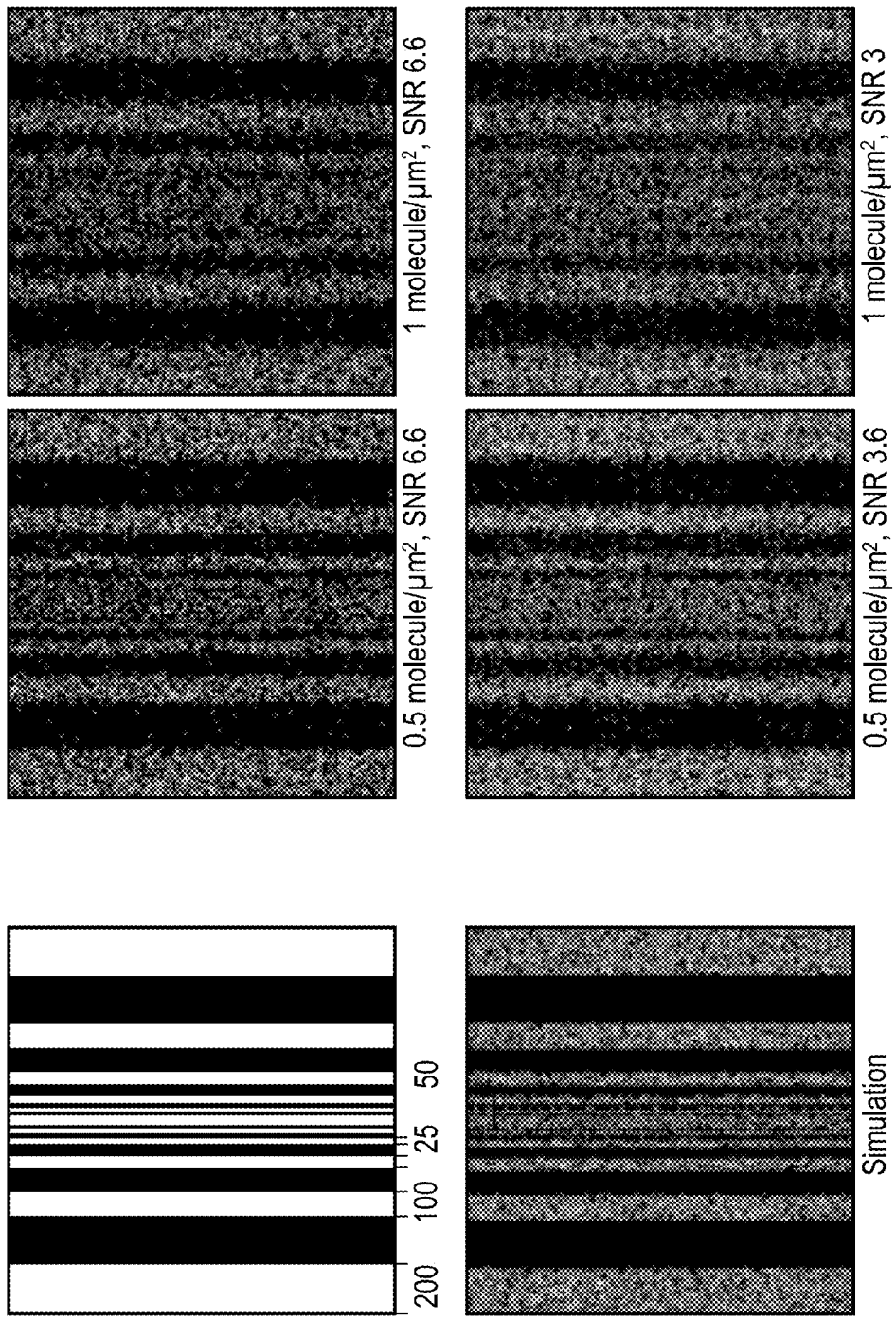
FIGS. 9A-9C illustrate tests of wavelet-based particle localization using simulated single-particle data inside a test pattern made of alternating stripes of variable width ranging from 200 nm (periphery) to 6 nm (center).
Figure 9C:
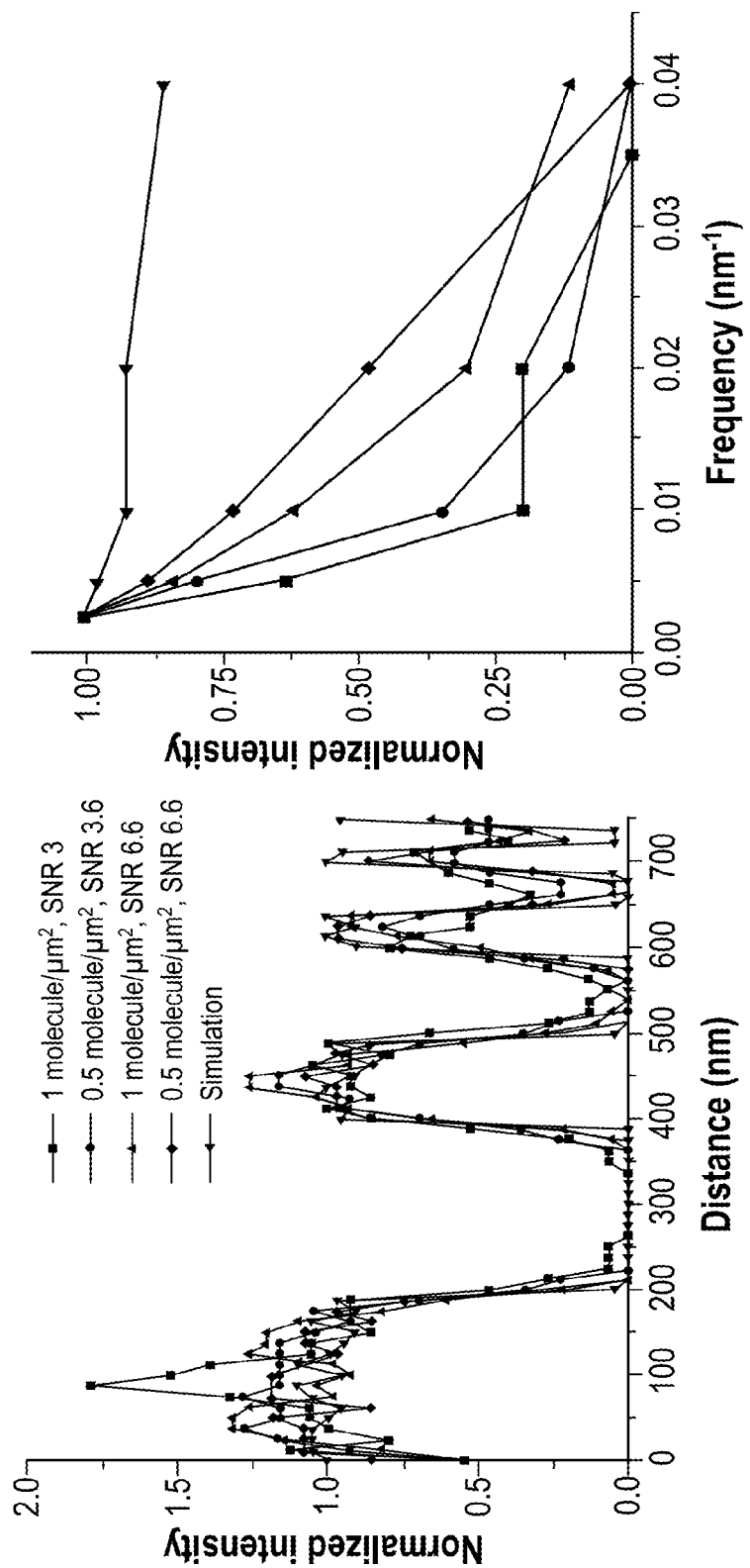

FIGS. 9A-9C illustrate simulations using a test pattern made of alternating black and white stripes of sizes ranging from 200 nm down to 6 nm in width. This type of test pattern has been widely used in radiology to determine the resolution of X-ray imaging systems. It can be used to visually monitor the segmentation performance and to compute the modulation transfer function (MTF) from the reconstructed image. The MTF(f) is calculated for each frequency f of the test pattern as the ratio C(f)/C(0), where C(f) is the contrast for the frequency f and C(0) is the contrast for low frequency.

FIG. 9A shows both the ideal simulated pattern (top) and a simulated pattern reconstructed from a limited number of particles (bottom). FIG. 9B shows reconstructed images after localization for various SNRs and particle densities. This simulation and analysis is of four different single-particle experiments in which the black stripes were populated with single particles at different densities and SNRs, from 0.5 particle/$\mu m^2$ and an SNR of 7.1 to 1 particle/$\mu m^2$ and an SNR of 3.1 using the protocol described above (FIGS. 9A and 9B).

FIG. 9C shows the contrast function (left) and the MTF(f) (right) for the simulations in FIGS. 9A and 9B. The resolution of the image is then estimated as the inverse of the cut-off-frequency (fc), obtained when the MTF(fc)=0 This representation validates the fact that lowering the SNR and increasing particle density from an ideal reference (e.g., a density of 0.5 particle/$\mu m^2$, SNR of 6.6, and resolution of about 25 nm) degrades the resolution of the super-resolution image. This is illustrated by a loss of contrast for the lines of 50 nm and even 100 nm in the case of 1 particle/$\mu m^2$ density and an SNR of 3. Beside its visual aspect, this representation complements the other simulations and does not require the knowledge of the coordinates of the source points, which makes it more suitable for performance testing. It also enables the quantification of the effect of the density of detected particles on the resolution, which affects single particle super-resolution microscopy. Even if this aspect has not been quantified in the current paper, it is evident that the limited number of particles affects the MTF of the simulated image.

Finally, TABLE 2 shows the results of a linear interpolation and cut-off frequency computation of the MTF on the first points where MTF(f)>15%, a threshold below which the contrast is noisy. The results in TABLE 2 agree with the resolutions computed in the simulation. The analysis with simulated data at different SNRs and molecular densities shows that the wavelet approach does not compromise the localization accuracy or the number of detected particles, compared to the classical Gaussian fit analysis, with an increase of up to a factor of 20 in the calculation speed.

TABLE 2

Localization Accuracy with Wavelet-Based Localization

| | SNR (Linear Units) | | | | |
|---|---|---|---|---|---|
| Density | 10.3 | 6.6 | 3.6 | 3.0 | 2.6 |
| 0.1 molecule/$\mu m^2$ | 9.2 nm | 13.4 nm | 28.9 nm | 37.2 nm | 47.6 nm |
| 0.25 molecule/$\mu m^2$ | 10.8 nm | 14.7 nm | 30.3 nm | 38.1 nm | 49 nm |
| 0.5 molecule/$\mu m^2$ | 13.2 nm | 17 nm (11.9 nm) | 31.8 nm (20.4 nm) | 39.6 nm | 50.3 nm |
| 0.75 molecule/$\mu m^2$ | 15.7 nm | 19.4 nm | 33.4 nm | 40.9 nm | 51.9 nm |
| 1 molecule/$\mu m^2$ | 18.4 nm | 22.2 nm (15.6 nm) | 35.4 nm | 42.4 nm (35.7 nm) | 54.8 nm |

2D Wavelet-Based Localization versus Gaussian Fitting with Experimental Data

Super-resolution imaging was performed on an inverted fluorescence microscope. Photoactivation was performed with a 405 nm laser and excitation with a 561 nm laser, both of them collimated into the microscope and focused at the rear plane of a high NA (1.49) 100× objective, therefore illuminating the sample in wide field configuration. The photon densities were 3×10$^{-2}$ kW/cm$^2$ (405 nm) and 4 kW/cm$^2$ (561 nm). Single particle signals were separated with a 561 nm dichroic and filtered with an emission filter centered at 617 nm and a spectral width of 70 nm. The signal was expanded with a 1.5× lens and focused on an EMCCD with pixel size of 16 μm, therefore the pixel size on the image plane was 107 nm. The low-resolution image of the pre-converted form of the fluorophore was taken using a mercury lamp for illuminations (excitation at 485 nm, emission at 525 nm).

Figure 10A:
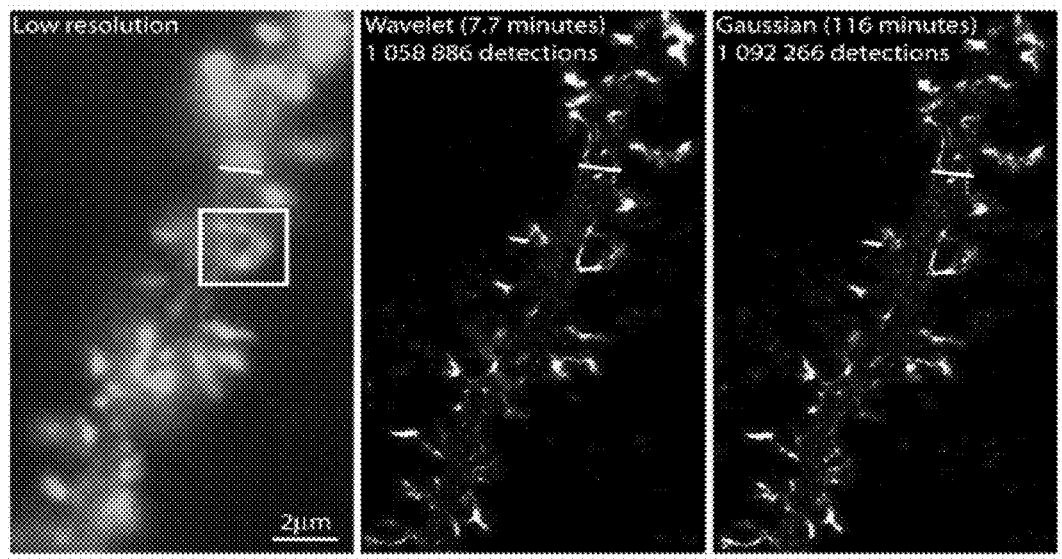
FIGS. 10A-10D show experimental data that illustrates performance of wavelet segmentation and the MTT algorithm with experimental PALM data.
Figure 10B:
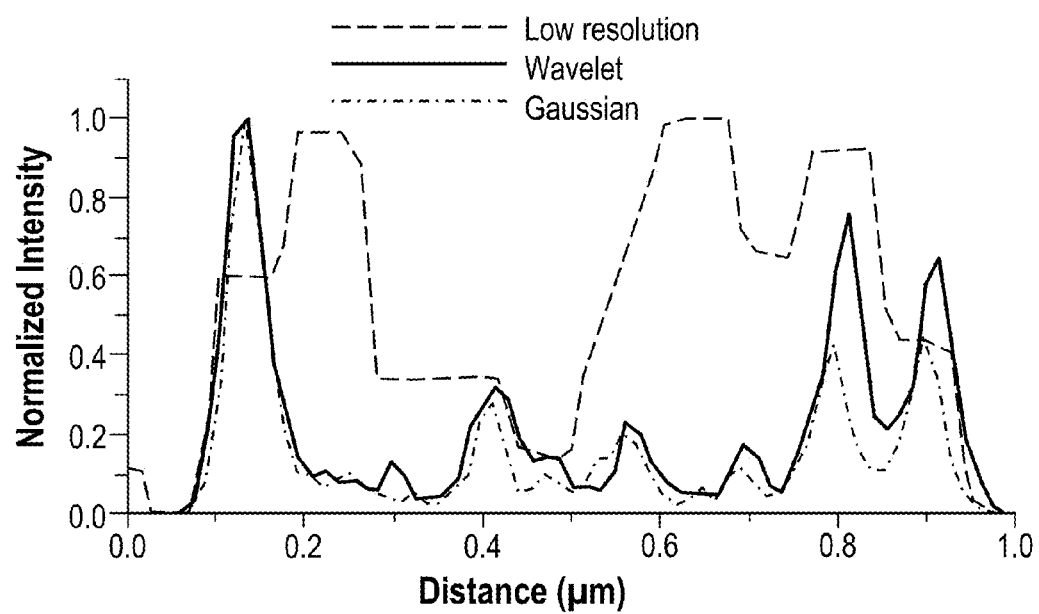
Figure 10C:
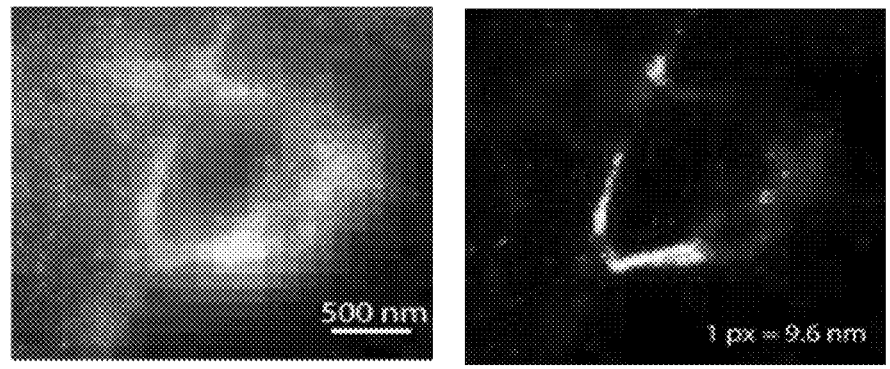

FIGS. 10A-10C show experimentally acquired images of the actin cytoskeleton of rat hippocampal neurons expressing ABP-tdEosFP and fixed with 4% paraformaldehyde processed with wavelet-based localization and Gaussian fitting. FIG. 10A shows a diffraction-limited preliminary snapshot (left) of the pre-converted form of the fluorophores. Subsequently, sparse subsets of single tdEosFP fluorophores were photoconverted and imaged until photobleached, recording a long-term acquisition of 50,000 frames of 50 ms (about 42 min of recording). These frames were processed with wavelet-based localization and Gaussian fitting to produce the super-resolution reconstructions at center and at right in FIG. 10A. The processing with the wavelet segmentation algorithm took 7.7 minutes and identified 1,058,886 single particle events, whereas the Gaussian approach took 116 minutes and detected 1,092,266 events. The reconstructed super-resolution images have the same resolution and no degradation of the image could be observed.

FIG. 10B shows intensity profile sections across the dendrite shaft (white line in FIG. 10A) for the low-resolution image and the super-resolution reconstructions performed with both wavelet segmentation and MTT. These super-resolution images were rendered by superimposing the position coordinates of the detected single particles, represented with a 2D Gaussian curve of unitary intensity value, with standard deviation determined by the mean localization accuracy of the detected particles.

The top panel of FIG. 10C shows the SNR of the detected fluorophores in a smaller region (box in FIG. 10A (left)) containing a single dendritic spine. The smaller region is about 2.65 µm×2.65 µm and contains an individual dendritic spine where 45,878 single particle events were detected with wavelet segmentation. The detected particles are overlaid with the diffraction limited image of the pre-converted fluorophores. The bottom panel of FIG. 10C shows a super-resolution reconstruction with a pixel size of 9.6 nm with each single particle represented by one pixel of unitary intensity.

Figure 10D:
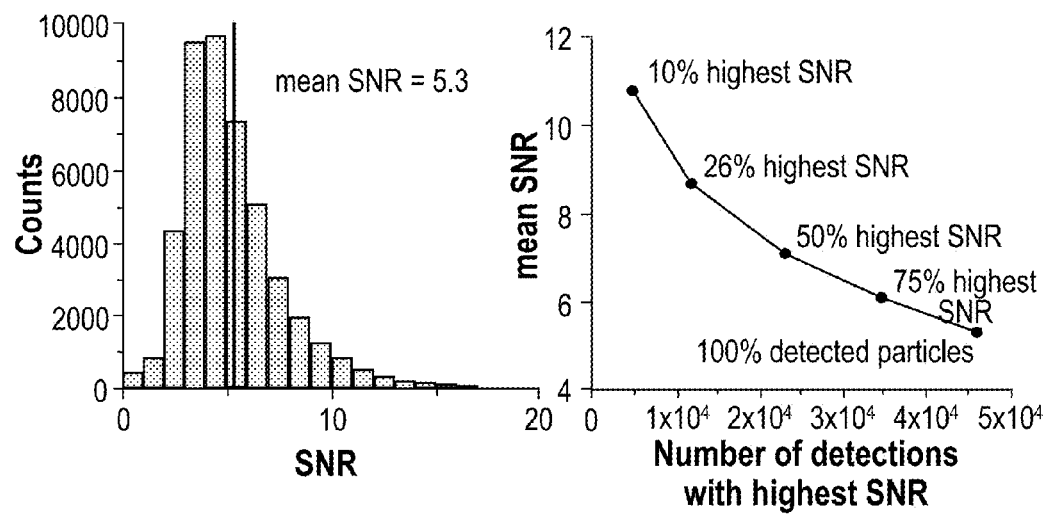

FIG. 10D is a histogram of the SNR values of the single fluorophore intensities detected in the region, with a mean SNR of 5.3, and the mean values of the SNR considering the brightest 10%, 25%, 50%, 75%, and 100% detections. More specifically, FIG. 10D shows the mean SNR of the distribution considering the brightest 10%, 25%, 50%, 75%, and 100% of all detected particles, corresponding to 4588, 11469, 22939, 34405, and 45878 detections, and a mean value of SNR of 10.8, 8.7, 7.1, 6.1, and 5.3, respectively.

Super-resolution optical microscopy based on single particle techniques may depend on the acquisition parameters and the image analysis among other things. More generally, super-resolution microscopy lacks real quantitative knowledge of the image resolution obtained with experimental data. In some cases, the spatial resolution has been either quantified on the data themselves, or determined using a theoretical framework. In techniques based on single-particle localization (e.g., PALM, STORM, and GSD), the resolution of the final reconstructed image depends on each individual particle's SNR, which may be proportional to the number of detected photons per particle, and the total particle density. The reconstructed image resolution can be regarded as the FWHM of the uncertainty distribution of the single particle position that is 2.4 times the pointing accuracy. Yet, a meaningful representation of the super-resolution image may require a minimum sampling, which translates into a minimum density of detected particles. The Nyquist-Shannon information sampling theorem states that a signal of bandwidth f can be reconstructed in its totality if this has been sampled with a frequency of 2 f. In the field of single particle-based super-resolution, a generalization of this theorem is commonly used in terms of image resolution and density of detected particles: the sampling of detected particles should be at least twice as dense as the image resolution.

In the case of biological experimental data, the SNR of all the detected particles can have a large distribution, as illustrated in FIG. 10D for the PALM representation of a dendritic spine. Given such broad distribution and the high density of single particle detections, one way of improving the resolution of the PALM reconstruction is to only consider the spots with the highest SNR, and rejecting those with a poor pointing accuracy that contribute to a loss in resolution. This a posteriori filtering may improve the final image resolution but at the expense of decreasing the density of particles, yet another limiting factor of the resolution. In practice, this imposes a minimum density of particles in order to reach a certain image resolution, independent of the localization accuracy of each individual particle. In the case of the individual spine of FIG. 10C, the detected actin particles are distributed in an area of 1 µm$^2$.

As a result, the resolution according to this generalization of the sampling theorem is 29.5 nm considering the brightest 10% of detections, 18.7 nm considering 25% of the brightest particles, 13.2 nm with 50%, 10.8 nm with 75%, and 9.3 nm with 100% of the detections. This resolution limit is given by the density of detected particles and not by the SNR of the detections. Therefore, for low densities the number of detected particles may define the maximal image resolution, whereas beyond that criterion, the SNR of the detections may be the limiting parameter. The balance between molecular density and a posteriori filtering of the data are two factors to consider when constructing a super-resolution image.

3D Wavelet-Based Particle Localization

FIGS. 11A and 11B are diffraction-limited images of tubulin labeled with Alexa647 fluorophore. FIG. 11C includes a series of diffraction-limited images showing the various orientations of single molecules. FIGS. 11D and 11E are dSTORM super-resolution intensity images constructed in real-time of the scenes shown in FIGS. 11A and 11B, respectively. FIGS. 11F and 11G show 3D mappings of the molecules shown in FIGS. 11D and 11E, respectively. These 3D mappings were generated after construction of the 2D super-resolution images shown in FIGS. 11D and 11E.

FIG. 11H is a plot of the calibration function (PSF) of the microscope used to extract the 3D position of individual molecules. The x axis represents the z distance measured from the nominal focal plane, and the y axis represent the full-width, half-maximum (sigma) of the Gaussian fit to the detected images. The inset images illustrate the appearance of the PSF at different distances from the focal plane. At negative distances from the nominal focal plane, the PSF appears to be roughly elliptical with the major axis aligned parallel to the x axis of the plot. The PSF's eccentricity decreases closer to the focal plane, then increases with positive distance from the nominal focal plane with the major axis aligned perpendicular to the x axis of the plot.

Figure 11:
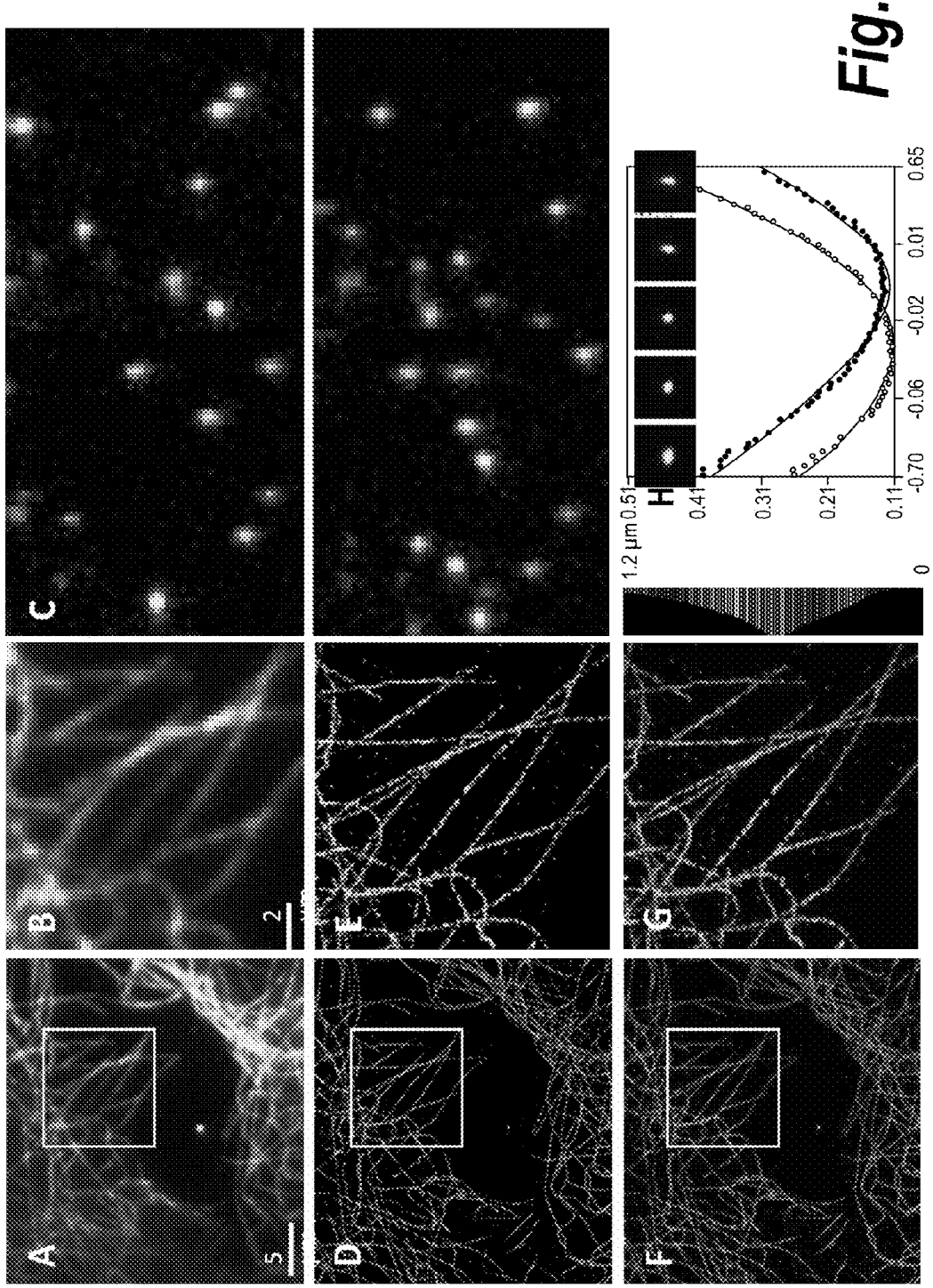
FIGS. 11A and 11B are diffraction-limited images of tubulin labeled with Alexa647 fluorophore.
FIG. 11C includes a series of diffraction-limited images showing the various orientations of single molecules of tubulin labeled with Alexa647 fluorophore.
FIGS. 11D and 11E are dSTORM super-resolution intensity images, constructed in real-time, of the molecules shown in FIGS. 11A and 11B, respectively.
FIGS. 11F and 11G show 3D mappings of the molecules shown in FIGS. 11D and 11E, respectively.
FIG. 11H is a plot of the calibration function (PSF) of the microscope used to extract the 3D positions of the individual molecules shown in FIGS. 11F and 11G.

The super-resolution images in FIG. 11 were obtained in real-time (2D) or near real-time (3D) using the wavelet segmentation and the Gaussian fitting described above. The images at far right show the microtubule organization at different planes with a lateral (x, y) resolution of 15 nm and an axial (z) resolution of 40 nm. The 2D super-resolution images could be observed in real-time during the streaming acquisition at 100 frames per seconds, while the 3D reconstruction of the 1.2 million particles was obtained within seconds to minutes after the acquisition. The image particle density was kept constant during the whole acquisition process by adjusting the 405 nm laser power during the acquisition.

Immunocytochemistry

COST cells plated on an 18 mm coverslip were fixed using 4% paraformaldehyde and sucrose and washed with PBS and then PBS containing 1% BSA. The washed cells were incubated with $NH_4Cl$ 50 mM for five minutes prior to permeabilization. They were permeabilized using 0.1% Triton and incubated with PBS containing 1% BSA for 30 minutes. They were then incubated with mouse-Anti-beta-tubulin antibody (T4026, Clone2.1, Sigma) for thirty minutes and washed several times with PBS containing 1% BSA. The primary antibodies were then revealed by incubating Alexa647 coupled anti-mouse IgG secondary (A21245, Invitrogen) for thirty minutes at room temperature.

Direct Stochastic Optical Reconstruction Microscopy

The stained coverslips were imaged the next day at room temperature in a closed chamber (Ludin Chamber, Life Imaging Services, Switzerland) mounted on an inverted motorized microscope (Nikon Ti, Japan) equipped with a 100×, 1.45 NA PL-APO objective and a perfect focus system, allowing long acquisition in oblique illumination mode. Imaging was performed in an extracellular solution containing reducing and oxygen scavenging system. For dSTORM, ensemble fluorescence of Alexa647 was first converted in to dark state using a 640 nm laser at 30-50 $kW/cm^2$ intensity. Once the ensemble fluorescence was converted into the desired density of single particles per frame, the laser power was reduced to 7-15 $kW/cm^2$ and imaged continuously at 50 fps for 20,000 frames. The level of single particles per frame was controlled by using a 405 nm laser (Omicron, Germany). The laser powers were adjusted to keep a specific level of stochastically activated particles which were well separated during the acquisition.

Both the ensemble and single particle fluorescence was collected by the combination of a dichroic and emission filter (D101-R561 and F39-617 respectively, Chroma, USA and quad-band dichroic filter (Di01-R405/488/561/635, Semrock, USA). The fluorescence was collected using a sensitive EM CCD (Evolve, Photometric, USA). The acquisition sequence was driven by Metamorph software (Molecular Devices, USA) in streaming mode at 50 frames per second (20 msec exposure time) using an area equal to or less than 256 pixel×256 pixel region of interest. Multicolour fluorescent microbeads (Tetraspeck, Invitrogen) were used to register long term acquisitions and correct for lateral drifts and chromatic shifts. A spatial resolution of 14 nm was measured using centroid determination on 100 nm Tetraspeck beads acquired with similar SNR as the dSTORM single-particle images.

Conclusion

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. For example, the embodiments may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

The memory may comprise any computer-readable media, and may store computer instructions (also referred to herein as "processor-executable instructions") for implementing the various functionalities described herein. The processing unit(s) (e.g., the CPU and the GPU) may be used to execute the instructions. Communication interface(s) may be coupled to a wired or wireless network, bus, or other communication means and may therefore allow the processor(s) and/or processing unit(s) to transmit communications to and/or receive communications from other devices. Display unit(s) may be provided, for example, to allow a user to view various information in connection with execution of the instructions. The user input device(s) may be provided, for example, to allow the user to make manual adjustments, make selections, enter data or various other information, and/or interact in any of a variety of manners with the processor during execution of the instructions.

The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, various inventive concepts may be embodied as a non-transitory computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

A flow diagram is used herein. The use of flow diagrams is not meant to be limiting with respect to the order of operations performed. The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations.

However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.).

It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrases "A or B" and "A and/or" will each be understood to include the possibilities of "A" or "B" or "A and B."

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. An apparatus for estimating a position of one or more particles, the apparatus comprising:
   an imaging system;
   a detector, in optical communication with the imaging system, configured to detect an image of a plane;
   a memory, operably coupled to the detector, configured to store a representation of the image; and
   a processor, operably coupled to the memory, configured to:
   (a) perform a wavelet decomposition of an image of the plane to form a wavelet map of the image;
   (b) segment the wavelet map into multiple regions having intensity values above a predetermined threshold; and
   (c) estimate the location of a centroid of at least one region, the location of the centroid corresponding to the position of the particle in a first dimension and a second dimension of the plane.

2. The apparatus of claim 1, wherein the particle includes at least one of a biological cell, a molecule, a fluorescent protein, an organic fluorophore, a quantum dot, a carbon nanotube, a diamond, a metal bead, a dielectric bead, and a particle tagged with a fluorophore.

3. The apparatus of claim 1, wherein the imaging system is characterized by a point spread function (PSF) that is asymmetric with respect to an optical axis of the imaging system.

4. The apparatus of claim 3, wherein the imaging system is an astigmatic imaging system.

5. The apparatus of claim 1, wherein the processor comprises a graphics processing unit (GPU) configured to perform at least one of (a), (b), and (c).

6. The apparatus of claim 1, wherein (a) comprises performing the wavelet decomposition à trous.

7. The apparatus of claim 1, wherein (b) comprises performing a watershed calculation of at least part of the wavelet map.

8. The apparatus of claim 1, wherein (b) further comprises:
   (i) determining a background noise level associated with the wavelet map;
   (ii) estimating a standard deviation associated with the background noise level; and
   (iii) selecting the predetermined threshold based on the standard deviation.

9. The apparatus of claim 8, wherein (iii) comprises selecting the predetermined threshold to be about 0.5 times to about 2.0 times the standard deviation.

10. The apparatus of claim 1, wherein (c) comprises estimating the location of the particle in the first dimension and the second dimension to a precision of about 1 nm to about 50 nm.

11. The apparatus of claim 1, wherein the processor is further configured to perform (a), (b), and (c) while the imaging system acquires another image.

12. The apparatus of claim 1, wherein the processor is further configured to:
    (d) perform a Gaussian fit initialized at the centroid position.

13. The apparatus of claim 12, wherein the processor is further configured to:
    (e) estimate the position of the particle in a third dimension from the Gaussian fit.

14. The apparatus of claim 13, wherein (e) comprises estimating the location of the particle in the third dimension to a precision of about 1 nm to about 50 nm.

15. The apparatus of claim 1, further comprising:
    a light source to excite the one or more particles, and
    wherein the processor is further configured to perform an analysis of the image and to adjust at least one of an intensity of the light source and a wavelength of the light source based on the analysis of the image.

16. The apparatus of claim 1, wherein the processor is further configured to perform an analysis of the image and to adjust at least one of a focus, a field of view, a frame size, a frame rate, and an integration time of the imaging system based on the analysis of the image.

17. A method of estimating a position of one or more particles, the method comprising:
    (a) performing a wavelet decomposition of an image of a plane to form a wavelet map of the image;
    (b) segmenting the wavelet map into multiples regions having intensity values above a predetermined threshold; and
    (c) estimating the location of a centroid of at least one region, the location of the centroid corresponding to the position of the particle in a first dimension and a second dimension of the plane.

18. The method of claim 17, wherein the particle includes at least one of a biological cell, a molecule, a fluorescent protein, an organic fluorophore, a quantum dot, a carbon nanotube, a diamond, a metal bead, a dielectric bead, and a particle tagged with a fluorophore.

19. The method of claim 17, wherein (a) comprises performing the wavelet decomposition à trous.

20. The method of claim 17, wherein (b) comprises performing a watershed calculation of at least part of the wavelet map.

21. The method of claim 17, wherein (b) further comprises:
    (i) determining a background noise level associated with the wavelet map;
    (ii) estimating a standard deviation associated with the background noise level; and
    (iii) selecting the predetermined threshold based on the standard deviation.

22. The method of claim 21, wherein (iii) comprises selecting the predetermined threshold to be about 0.5 times to about 2.0 times the standard deviation.

23. The method of claim 17, wherein (c) comprises estimating the location of the particle in the first dimension and the second dimension to a precision of about 1 nm to about 50 nm.

24. The method of claim 17, further comprising:
    (d) determining a fit of a point spread function (PSF) of an imaging system to the at least one region.

25. The method of claim 24, further comprising:
(e) estimating the position of the particle, in a third dimension, from the fit.

26. The method of claim 25, wherein (e) comprises estimating the location of the particle in the third dimension to a precision of about 1 nm to about 50 nm.

27. The method of claim 25, wherein the PSF is asymmetric with respect to the third dimension, and further comprising, before (a):
acquiring the image with the imaging system characterized by the PSF.

28. The method of claim 25, wherein the imaging system is an astigmatic imaging system.

29. The method of claim 17, further comprising:
acquiring a plurality of images, wherein each image in the plurality of images corresponds to a different plane of a three-dimensional (3D) space; and
performing steps (a), (b), and (c) for each image in the plurality of images.

30. The method of claim 29, further comprising:
acquiring another image of another plane in the 3D space while performing at least one of steps (a), (b), and (c).

31. The method of claim 17, further comprising:
performing an analysis of the image; and
adjusting at least one of a focus, a field of view, a frame size, a frame rate, and an integration time of an imaging system based on the analysis of the image.

32. The method of claim 17, wherein the image represents fluorescent emission by the one or more particles, and further comprising:
performing an analysis of the image; and
adjusting at least one of an intensity of the light source and a wavelength of the light source used to excite the fluorescence emission based on the analysis of the image.

33. A non-transitory computer program product, which, when executed by a processor, causes the processor to:
(a) perform a wavelet decomposition of an image of a plane to form a wavelet map of the image;
(b) segment the wavelet map into multiple regions having intensity values above a predetermined threshold; and
(c) estimate the location of a centroid of at least one region, the location of the centroid corresponding to the position of a particle in a first dimension and a second dimension.

* * * * *